United States Patent
Kaplan et al.

(10) Patent No.: US 10,339,781 B2
(45) Date of Patent: Jul. 2, 2019

(54) METHODS AND APPARATUS FOR MONITORING ALTERNESS OF AN INDIVIDUAL UTILIZING A WEARABLE DEVICE AND PROVIDING NOTIFICATION

(71) Applicant: Torvec, Inc., Rochester, NY (US)

(72) Inventors: Richard A. Kaplan, Rochester, NY (US); Douglas A. Hemink, Churchville, NY (US); Matt Kenyon, Spencerport, NY (US)

(73) Assignee: CurAegis Technologies, Inc., Rochester, NY (US)

( * ) Notice: Subject to any disclaimer, the term of this patent is extended or adjusted under 35 U.S.C. 154(b) by 0 days.

(21) Appl. No.: 16/035,971

(22) Filed: Jul. 16, 2018

(65) Prior Publication Data

US 2018/0342143 A1 Nov. 29, 2018

Related U.S. Application Data

(63) Continuation of application No. 15/510,031, filed as application No. PCT/US2015/048881 on Sep. 8, 2015, now Pat. No. 10,055,964.

(Continued)

(51) Int. Cl.
*G08B 21/06* (2006.01)
*G08B 21/04* (2006.01)
(Continued)

(52) U.S. Cl.
CPC .......... *G08B 21/06* (2013.01); *A61B 5/02055* (2013.01); *A61B 5/0456* (2013.01);
(Continued)

(58) Field of Classification Search
CPC ............ A61B 5/1118; A61B 2562/046; G01N 2203/0073; A61K 9/0009
See application file for complete search history.

(56) References Cited

U.S. PATENT DOCUMENTS 509,791 A 11/1893 Callender
600,806 A 3/1898 Scott
(Continued)

FOREIGN PATENT DOCUMENTS

CN 202443558 U 9/2012
CN 102881117 A 1/2013
(Continued)

OTHER PUBLICATIONS

International Search Report dated Nov. 24, 2015 for International Application No. PCT/US2015/048881.
(Continued)

*Primary Examiner* — Fabricio R Murillo Garcia
(74) *Attorney, Agent, or Firm* — Dinsmore & Shohl LLP

(57) ABSTRACT

Methods and apparatus for monitoring fatigue and notifying an individual are described. The individual may be an operator of a vehicle, equipment, or machine, a student, or other person that may experience fatigue. Motion of the individual is monitored to detect a predescribed motion in response to a stimulus to first determine a base responsiveness profile. Afterwards, a current responsiveness profile is determined based on a prescribed motion in response to a stimulus, and if the current responsiveness profile exceeds a predetermined threshold of the base responsiveness profile, a notification is issued to the individual and, optionally, another person such as an employer, teacher, or parent.

33 Claims, 12 Drawing Sheets

Related U.S. Application Data

(60) Provisional application No. 62/047,893, filed on Sep. 9, 2014, provisional application No. 62/155,124, filed on Apr. 30, 2015.

(51) Int. Cl.

| | | |
|---|---|---|
| G06F 19/00 | (2018.01) | |
| A61B 5/00 | (2006.01) | |
| A61B 5/0456 | (2006.01) | |
| G08B 25/01 | (2006.01) | |
| B60W 40/08 | (2012.01) | |
| B60K 28/06 | (2006.01) | |
| A61B 5/18 | (2006.01) | |
| A61B 5/16 | (2006.01) | |
| A61B 5/0205 | (2006.01) | |
| A61B 5/024 | (2006.01) | |
| A61B 5/053 | (2006.01) | |
| A61B 5/11 | (2006.01) | |

(52) U.S. Cl.
CPC .......... *A61B 5/1104* (2013.01); *A61B 5/162* (2013.01); *A61B 5/18* (2013.01); *A61B 5/6801* (2013.01); *A61B 5/6831* (2013.01); *A61B 5/7275* (2013.01); *A61B 5/74* (2013.01); *A61B 5/742* (2013.01); *A61B 5/7405* (2013.01); *A61B 5/7455* (2013.01); *B60K 28/066* (2013.01); *B60W 40/08* (2013.01); *G06F 19/00* (2013.01); *G08B 21/0446* (2013.01); *G08B 21/0453* (2013.01); *G08B 25/016* (2013.01); *A61B 5/024* (2013.01); *A61B 5/02416* (2013.01); *A61B 5/0533* (2013.01); *A61B 5/1112* (2013.01); *A61B 2560/0242* (2013.01); *A61B 2562/0219* (2013.01); *G08B 21/043* (2013.01)

(56) References Cited

U.S. PATENT DOCUMENTS

| | | |
|---|---|---|
| 2,875,430 A | 2/1959 | Kayser, Jr. |
| 3,186,508 A | 6/1965 | Lamont |
| 3,222,639 A | 12/1965 | Kayser, Jr. |
| 3,222,640 A | 12/1965 | Wurst |
| 3,223,998 A | 12/1965 | Hose |
| 3,524,030 A | 8/1970 | Wiegel |
| 3,631,446 A | 12/1971 | Setser |
| 3,654,599 A | 4/1972 | Sepper |
| 3,861,349 A | 1/1975 | Conley |
| 3,935,830 A | 2/1976 | Cox |
| 3,972,038 A | 7/1976 | Fletcher et al. |
| 3,980,999 A | 9/1976 | Nishioka |
| 4,007,357 A | 2/1977 | Yanagishima |
| 4,017,843 A | 4/1977 | Yanagishima |
| 4,059,830 A | 11/1977 | Threadgill |
| 4,104,621 A | 8/1978 | Yanagishima |
| 4,354,179 A | 10/1982 | Fourcade |
| 4,359,725 A | 11/1982 | Balogh et al. |
| 4,361,834 A | 11/1982 | King |
| 4,365,637 A | 12/1982 | Johnson et al. |
| 4,450,438 A | 5/1984 | Seko et al. |
| 4,463,347 A | 7/1984 | Seko et al. |
| 4,496,938 A | 1/1985 | Seko et al. |
| 4,509,531 A | 4/1985 | Ward |
| 4,518,954 A | 5/1985 | Seko et al. |
| 4,519,040 A | 5/1985 | Brankamp et al. |
| 4,564,833 A | 1/1986 | Seko |
| 4,564,993 A | 1/1986 | Blaurock et al. |
| 4,581,617 A | 4/1986 | Yoshimoto et al. |
| 4,586,032 A | 4/1986 | Seko et al. |
| 4,586,827 A | 5/1986 | Hirsch et al. |
| 4,594,583 A | 6/1986 | Seko et al. |
| 4,604,617 A | 8/1986 | Morozumi |
| 4,611,199 A | 9/1986 | Seko et al. |
| 4,673,913 A | 6/1987 | Akita et al. |
| 4,706,072 A | 11/1987 | Ikeyama |
| 4,794,536 A | 12/1988 | Eto et al. |
| 4,819,860 A | 4/1989 | Hargrove et al. |
| 4,853,672 A | 8/1989 | Yasuda et al. |
| 4,928,090 A | 5/1990 | Yoshimi et al. |
| 4,984,646 A | 1/1991 | Sano et al. |
| 4,996,647 A | 2/1991 | Gasser |
| 5,057,834 A | 10/1991 | Nordstrom |
| 5,259,390 A | 11/1993 | MacLean |
| 5,282,135 A | 1/1994 | Sato et al. |
| 5,311,877 A | 5/1994 | Kishi |
| 5,402,109 A | 3/1995 | Mannik |
| 5,465,079 A | 11/1995 | Bouchard et al. |
| 5,488,353 A | 1/1996 | Kawakami et al. |
| 5,497,779 A | 3/1996 | Takaya et al. |
| 5,515,858 A | 5/1996 | Myllymaeki |
| 5,548,773 A | 8/1996 | Kemeny et al. |
| 5,568,127 A | 10/1996 | Bang |
| 5,570,087 A | 10/1996 | Lemelson |
| 5,570,698 A | 11/1996 | Liang et al. |
| 5,585,785 A | 12/1996 | Gwin et al. |
| 5,670,944 A | 9/1997 | Myllymaeki |
| 5,684,455 A | 11/1997 | Williams et al. |
| 5,684,462 A | 11/1997 | Gold |
| 5,689,241 A | 11/1997 | Clarke et al. |
| 5,694,116 A | 12/1997 | Kojima |
| 5,709,281 A | 1/1998 | Sherwin et al. |
| 5,714,925 A | 2/1998 | Lee et al. |
| 5,717,606 A | 2/1998 | Hara et al. |
| 5,729,619 A | 3/1998 | Puma |
| 5,745,031 A | 4/1998 | Yamamoto |
| 5,765,116 A | 6/1998 | Wilson et al. |
| 5,786,765 A | 7/1998 | Kumakura et al. |
| 5,795,306 A | 8/1998 | Shimotani et al. |
| 5,798,695 A | 8/1998 | Metalis et al. |
| 5,805,079 A | 9/1998 | Lemelson et al. |
| 5,805,720 A | 9/1998 | Suenaga et al. |
| 5,813,989 A | 9/1998 | Saitoh et al. |
| 5,813,993 A | 9/1998 | Kaplan et al. |
| 5,815,070 A | 9/1998 | Yoshikawa et al. |
| 5,821,860 A | 10/1998 | Yokoyama et al. |
| 5,835,008 A | 11/1998 | Colemere |
| 5,835,028 A | 11/1998 | Bender et al. |
| 5,847,648 A | 12/1998 | Savor et al. |
| 5,850,193 A | 12/1998 | Shimoura et al. |
| 5,867,587 A | 2/1999 | Aboutalib et al. |
| 5,900,819 A | 5/1999 | Kyrtsos |
| 5,907,282 A | 5/1999 | Tuorto et al. |
| 5,917,415 A | 6/1999 | Atlas |
| 5,923,263 A | 7/1999 | Rodriguez |
| 5,925,082 A | 7/1999 | Shimizu et al. |
| 5,939,989 A | 8/1999 | Bang |
| 5,942,979 A | 8/1999 | Luppino |
| 5,969,616 A | 10/1999 | Tschoi et al. |
| 5,982,287 A | 11/1999 | Brannen et al. |
| 5,990,795 A | 11/1999 | Miller |
| 6,023,227 A | 2/2000 | Yanko et al. |
| 6,061,610 A | 5/2000 | Boer |
| 6,064,301 A | 5/2000 | Takahashi et al. |
| 6,067,020 A | 5/2000 | Wimmer et al. |
| 6,087,641 A | 7/2000 | Kinouchi et al. |
| 6,087,943 A | 7/2000 | Bailey |
| 6,091,334 A | 7/2000 | Galiana et al. |
| 6,097,286 A | 8/2000 | Discenzo |
| 6,097,295 A | 8/2000 | Griesinger et al. |
| 6,172,610 B1 | 1/2001 | Prus |
| 6,184,791 B1 | 2/2001 | Baugh |
| 6,195,165 B1 | 2/2001 | Sayegh |
| 6,265,978 B1 | 7/2001 | Atlas |
| 6,313,749 B1 | 11/2001 | Horne et al. |
| 6,353,396 B1 | 3/2002 | Atlas |
| 6,545,607 B2 | 4/2003 | Bredow et al. |
| 6,686,845 B2 | 2/2004 | Oyama |
| 6,756,903 B2 | 6/2004 | Omry et al. |
| 6,762,684 B1 | 7/2004 | Camhi |
| 6,791,462 B2 | 9/2004 | Choi |
| 6,822,573 B2 | 11/2004 | Basir et al. |

(56) References Cited

U.S. PATENT DOCUMENTS

| | | |
|---|---|---|
| 6,950,027 B2 | 9/2005 | Banas |
| 7,019,623 B2 | 3/2006 | Klausner et al. |
| 7,084,773 B2 | 8/2006 | Oyama |
| 7,602,278 B2 | 10/2009 | Prost-Fin et al. |
| 7,605,694 B2 | 10/2009 | Prost-Fin et al. |
| 7,692,552 B2 | 4/2010 | Harrington et al. |
| 7,830,265 B2 | 11/2010 | Power |
| 7,839,292 B2 | 11/2010 | Wang et al. |
| 7,898,426 B2 | 3/2011 | Rai et al. |
| 7,956,757 B2 | 6/2011 | Kumar et al. |
| 8,033,916 B2 | 10/2011 | Caldwell et al. |
| 8,123,624 B2 | 2/2012 | Caldwell |
| 8,188,870 B2 | 5/2012 | Kumar et al. |
| 8,199,018 B2 | 6/2012 | Shigetou |
| 8,303,172 B2 | 11/2012 | Zei et al. |
| 8,339,268 B2 | 12/2012 | Deng et al. |
| 8,356,899 B2 | 1/2013 | Hirata |
| 8,439,686 B2 | 5/2013 | Zayfert et al. |
| 8,491,397 B2 | 7/2013 | Caldwell et al. |
| 8,604,932 B2 | 12/2013 | Breed et al. |
| 8,698,635 B2 | 4/2014 | Sullivan et al. |
| 8,725,311 B1 | 5/2014 | Breed |
| 8,742,936 B2 | 6/2014 | Galley et al. |
| 8,773,269 B2 | 7/2014 | Richardson et al. |
| 8,812,428 B2 | 8/2014 | Mollicone et al. |
| 8,823,527 B2 | 9/2014 | Husen et al. |
| 2004/0044293 A1 | 3/2004 | Burton |
| 2004/0145493 A1 | 7/2004 | O'Connor et al. |
| 2005/0070824 A1 | 3/2005 | Rhad et al. |
| 2006/0282021 A1 | 12/2006 | DeVaul et al. |
| 2007/0167850 A1 | 7/2007 | Russell et al. |
| 2008/0174451 A1 | 7/2008 | Harrington et al. |
| 2008/0180235 A1 | 7/2008 | Chang |
| 2008/0266118 A1 | 10/2008 | Pierson et al. |
| 2009/0189772 A1 | 7/2009 | Christ et al. |
| 2009/0268022 A1 | 10/2009 | Omi |
| 2009/0273478 A1 | 11/2009 | Mei |
| 2010/0100004 A1 | 4/2010 | van Someren |
| 2010/0137748 A1 | 6/2010 | Sone et al. |
| 2011/0077548 A1 | 3/2011 | Torch |
| 2011/0080285 A1 | 4/2011 | Howson et al. |
| 2011/0175726 A1 | 7/2011 | Baird et al. |
| 2012/0007735 A1 | 1/2012 | Rhyins |
| 2012/0191425 A1* | 7/2012 | Mott ............... A61B 5/16 703/2 |
| 2012/0316456 A1 | 12/2012 | Rahman et al. |
| 2013/0018284 A1 | 1/2013 | Kahn et al. |
| 2013/0120106 A1 | 5/2013 | Cauwels et al. |
| 2014/0077957 A1 | 3/2014 | Bichara |
| 2014/0081179 A1* | 3/2014 | Moore-Ede ........ A61B 5/1118 600/595 |
| 2014/0085077 A1 | 3/2014 | Luna et al. |
| 2014/0253325 A1 | 9/2014 | Ky |
| 2015/0109124 A1 | 4/2015 | He et al. |
| 2015/0148616 A1* | 5/2015 | Van Dongen ........ G16H 50/30 600/300 |
| 2015/0186594 A1 | 7/2015 | Zhang et al. |
| 2015/0223743 A1 | 8/2015 | Pathangay et al. |
| 2015/0313529 A1 | 11/2015 | Nevo et al. |

FOREIGN PATENT DOCUMENTS

| | | |
|---|---|---|
| CN | 202929361 U | 5/2013 |
| CN | 203552404 U | 4/2014 |
| CN | 102881117 B | 11/2014 |
| DE | 10041116 A1 | 7/2001 |
| EP | 793582 A1 | 9/1997 |
| EP | 853559 A4 | 7/2000 |
| EP | 853559 A1 | 3/2002 |
| EP | 853559 B1 | 3/2002 |
| GB | 2334127 A | 8/1999 |
| GB | 2375645 A | 11/2002 |
| GB | 2375645 A8 | 3/2004 |
| WO | 200854460 A2 | 5/2008 |
| WO | 2008054460 A3 | 6/2008 |
| WO | 2012144948 A1 | 10/2012 |
| WO | 2016019002 A1 | 2/2016 |

OTHER PUBLICATIONS

International Preliminary Report and Written Opinion dated Mar. 23, 2017 for International Application No. PCT/US2015/048881.
2014 Bluetooth Watch New Wearable Electronic Device L12 Wristband NFC Handsfree Car Kit Wireless Smart Watch for iPhone, Nov. 13, 2014, pp. 1-6, retrieved from http://smartfly.en.alibaba.com/Handsfree_Car_Kit_Wireless_Smart_Watch_for_iphone.html.
Brunel University London, Brunel Students Design Set to Reduce Number of Crashes on our Roads, Press Release May 25, 2006, p. 1, retrieved from http://www.brunel.ac.uk/news-and-events/news/news-items/press/ne_24830.
Caterppillar, Operator Fatigue Detection Technology Review, 2008, pp. 1-58, retrieved from https://safety.cat.com/cda/files/771871/7/fatigue_report_021108.pdf.
Cinaz, B. et al., A Wearable User Interface for Measuring Reaction Time, Ambient Intelligence, 2011, pp. 1-10.
Fatigue Science, The Readiband System, Nov. 13, 2014, pp. 1-3, retrieved from http://fatiguescience.com/solutions/readiband/.
Fitness Wristbands Manufacturer, Fitness Wristbands with Pedometer/Sleep Mnitor Calorie counter/Waterproof Function, Nov. 13, 2014, pp. 1-3, retrieved from http://www.globalsources.com/gsol/I/Smart-bracelet/p/sm/1107796260.htm#1107796260.
Horsey, Julian, Geeky Gadgets, Stay Awake and Focused During the Day Using the Spark Watch, Jul. 7, 2014, pp. 1-4, retrieved from http://www.geeky-gadgets.com/stay-awake-and-focused-during-the-day-using-the-spark-watch-07-07-2014/.
Huayang, HuaYang Fashion Movement Monitoring Tracking Fatigue Remind 4.0 Bluetooth Bracelet Wristband, Jul. 8, 2014, p. 1-3, retrieved from http://www.amazon.co.uk/HuaYang-Movement-Monitoring-Bluetooth-Wristband/dp/B00LLV2Q7M.
Ivorra, A. et al., Minimally Obtrusive Wearable Device for Continuous Interactive Cognitive and Neurological Assessment, Physiol MEas, 2008, pp. 1-14.
Neurontools, Attention Meter, Nov. 13, 2014, pp. 1-2, retrieved from http://www.neurontools.com/attention_meter.html.
Pedley, Mark, Tilt Sensing Using a Three-Axis Accelerometer, Freescale Semiconductor, Document No. AN3461 Revision 6, Mar. 2013, pp. 1-22.
Rideroom, Driver-Fatigue Bracelet, May 16, 206, pp. 1-2, retrieved from http://www.rideroom.com/news_comments.php?id=2389.
ISR/WO issued in corresponding PCT Application No. PCT/US2017/018355, dated May 15, 2017 (May 15, 2017).
Non-Final Office Action in related U.S. Appl. No. 15/436,039 dated Oct. 4, 2017 (15 pages total).

* cited by examiner

METHODS AND APPARATUS FOR MONITORING ALERTNESS OF AN INDIVIDUAL UTILIZING A WEARABLE DEVICE AND PROVIDING NOTIFICATION

CROSS REFERENCE TO RELATED APPLICATIONS

This application is a continuation application of U.S. application Ser. No. 15/510,031, filed Mar. 9, 2017, which is a National Stage application of PCT/US2015/048881, filed Sep. 8, 2015, which claims priority from U.S. Provisional Application No. 62/047,893, filed Sep. 9, 2014, and from U.S. Provisional Application No. 62/155,124, filed Apr. 30, 2015, which applications are incorporated by reference herein in their entirety.

BACKGROUND OF THE INVENTION

Lack of alertness due to operator fatigue is a major cause of job failure and accidents such as in moving vehicles. Numerous efforts have been made to monitor operator fatigue, especially for long haul trucking where even a momentary lapse of consciousness can lead to catastrophic loss of life and property. These efforts typically visually monitor the operator and/or require the operator to perform a task, such as striking a button on the dashboard. Such techniques are often expensive and/or ineffective.

Alertness may also adversely affect other individuals such as students and workers. When alertness diminishes in fatigued individuals, these individuals may not be able to stay awake. Techniques for monitoring and assisting such individuals are desirable.

SUMMARY OF THE INVENTION

Methods, systems, and apparatus for monitoring alertness (e.g., a degradation in alertness) and providing notification based on the monitored alertness are described. The methods, systems, and apparatus may use a holistic approach to monitoring and estimating an Individual's alertness over time, incorporating both passive and active measurements of the individual. The passive and active measurements may also include objective and subjective components to assess the individual's overall alertness or risk of falling asleep. Combinations of passive, active, objective, and subjective measurements may be used to create cumulative assessments of the individual's risk for failing asleep or reaching dangerous levels of fatigue. The methods, systems, and apparatus may also be useful in mitigating dangers resulting from an individual's fatigue or lack of alertness.

Lack of alertness may be due to fatigue, boredom, inattentiveness, drug use, sickness, etc. The individual being monitored may be an operator of a vehicle, equipment, or machine; a student; or other person that may experience fatigue. By way of non-limiting example, these individuals may be truck drivers, general public drivers, airline pilots, train engineers, school and over the road bus drivers, security guards, store clerks, children, the elderly, campers, hunters, hikers, surveillance agents, students, military personnel, business people (e.g., for use in meetings, training classes, etc.), people with health problems. The methods, systems, and apparatus may be employed in, by way of non-limiting example, "man down" systems, security systems, etc. In addition to the individual, essentially any entity may be notified regarding the monitored individual, e.g., another person such as an employer, teacher, or parent; an automated system; a computer system; a computer application; etc.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Aspects of the invention provide an improved means of monitoring the alertness (e.g., lack and/or degradation of alertness) of an individual or user such as an operator of a vehicle, equipment, or machine, e.g., by monitoring the operator's movement and, notifying an entity when there is a discernible lack of response, diminished range of movement, and/or diminished reaction time. Aspects described herein also incorporate passive and active measurements of a user to holistically monitor and estimate the user's alertness. The passive and active measurements may be combined and processed to determine overall alertness risks. The holistic monitoring apparatus, systems, and methods embodied herein by aspects may also adjust the estimated alertness of an user over time as a result of the passive and active measurements. The passive and active measurements may include both subjective and objective components.

The system may be tied into other systems such as, for example, a telematics system, e.g., for long haul trucking in order to notify the dispatcher that the operator is reaching a potentially dangerous level of fatigue and needs to rest. Aspects described herein may be used to monitor users such as, for example, truck drivers, general public drivers, airline pilots, train engineers, school and over the road bus drivers, security guards, store clerks, children, the elderly, campers, hunters, hikers, surveillance agents, students, military personnel, business people (e.g., for use in meetings, training classes, etc.), people with health problems and notify them and/or another entity when there is a determination of a lack of alertness (e.g., diminished response, diminished range, and/or lack of movement, for example, due to fatigue, boredom, having fallen asleep, etc.).

Figure 1A:
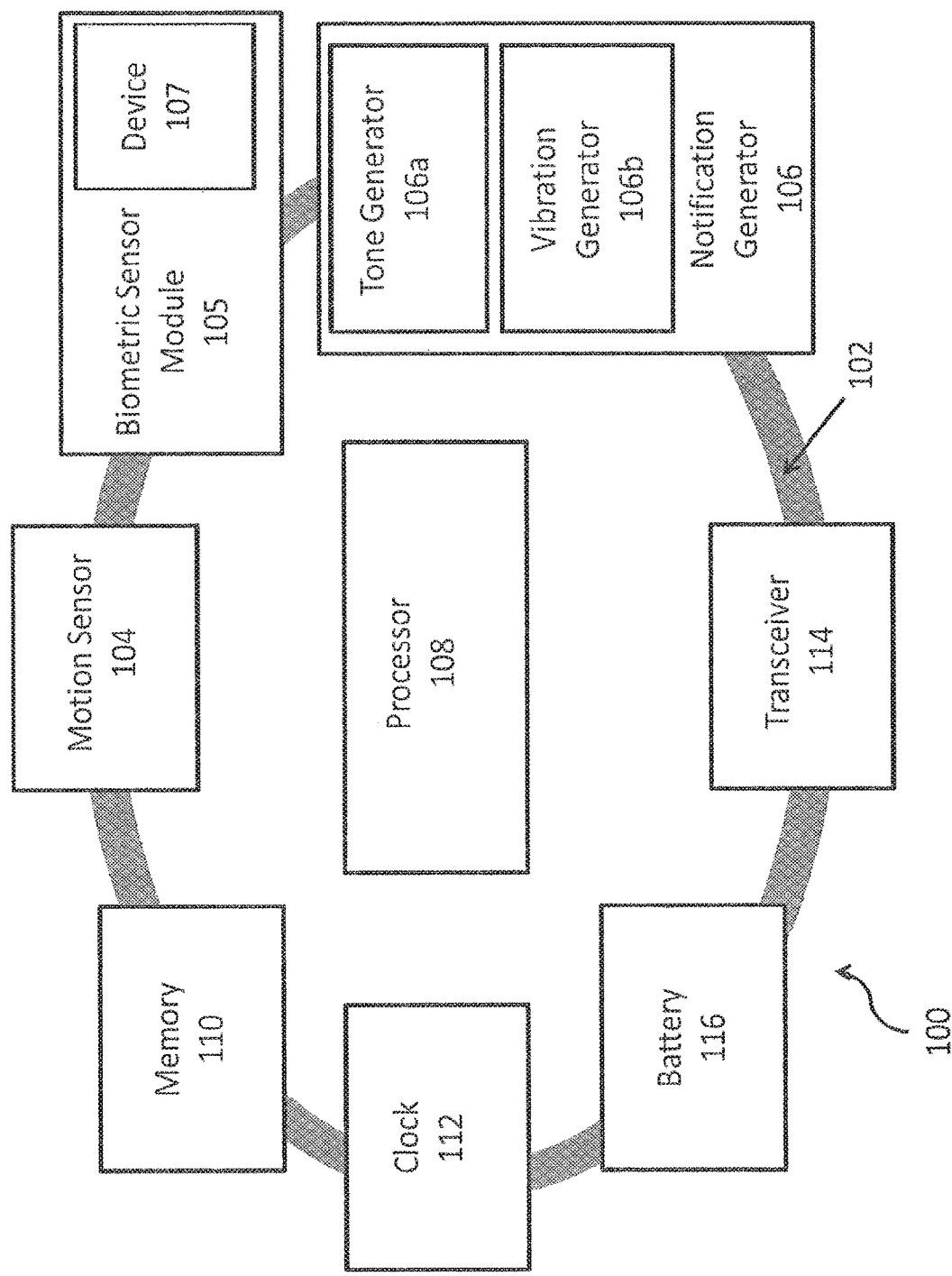
FIGS. 1A and 1B are block diagrams of wearable apparatuses in accordance with aspects of the present invention.

FIG. 1A depicts a wearable apparatus 100 for monitoring alertness and providing a notification, e.g., to the user wearing the apparatus and/or to another entity. The illustrated wearable apparatus 100 is embodied in a band 102, which may be placed on the user's wrist, for example. The band 102 supports at least one motion sensor 104 and at least one biometric sensor module 105 for monitoring the user and at least one notification generator 106 (e.g., tone generator 106a, vibration generator 106b, and visual generator 106c) for providing notifications to an entity, e.g., reminders and/or alerts (such as warnings and/or alarms). The tone generator 106a may be an audio tone generator and the vibration generator 106b may be an offset weight spinner. Additionally, the notification generator (106) may issue a notification to be transmitted via a transceiver 114 to another entity at a remote location, such as a third party. The third party recipient of the notification would then be apprised of any reminders, alerts, or alarms issued to the user, much like a silent alarm. Suitable motion sensors 104, biometric sensor modules 105, and generators 106 for use with the present invention will be understood by one of skill in the art from the description herein.

The motion sensor 104 may include one or more gyroscopes and/or accelerometers to track movements (linear, angular, etc.). The movements monitored or tracked may include prescribed motions of the user, other movements by the user outside of prescribed motions, the user's relative motion, or motion caused by the user's environment (such as vibration from a truck engine, etc.). In addition to measuring movement, the motion sensor 104 may be used to estimate the user's body position (e.g. sitting, standing, lying down). The motion sensor 104 can be used for passive measurements (defined as those measurements that can be made merely by having the user wear the apparatus 100) and active measurements (defined as those measurements that require the user to actively perform a task or input data while wearing the apparatus 100).

Techniques for tracking movements and/or body position is through accelerometers and/or gyroscopes. There are many small, low-power gyroscopes available on the market. The gyroscopes typically employ piezoelectric sensors or other forms of micro-electronic motion sensors (MEMS). For instance, SGS-Thompson Microelectronics (st.com) has a line of MEMS based gyroscopes that operate on low power, measure all three axes of movement, provide digital output that can be fed directly into a microprocessor, and that have a low noise threshold and low gyroscopic drift, allowing them to measure the fine movements with high precision and repeatability. The L3G3200D is a suitable device having an operational voltage range from 2.4V to 3.6V, which is well suited for battery operation, consumes only 6.1 mA in typical operation, has an operating range of −40 to +85 degrees Celsius, Includes an embedded temperature sensor, and has digital output of both temperature and angular rates of movement, with up to 16-bits of precision for angular rates.

As an alternative to a MEMS gyroscopes, linear accelerometers may be used. Since MEMS linear accelerometers respond to the gravitational field as well as linear acceleration, when arranged in a three-axis configuration, it is possible to compute rotational changes to yaw, pitch, and roll, as described in the paper "Tilt Sensing Using a Three-Axis Accelerometer," by Mark Pedley; Freescale Semiconductor, Document Number AN3461, Revision 6, March 2013, which is incorporated fully herein by reference.

The biometric sensor module 105 may include one or more sensors to measure one or more biomarkers of the user. Biomarkers that may be measured in accordance with aspects of this invention include, but are not limited to, skin temperature, heart-related metrics, galvanic skin response, power exerted by a body part, skin resistivity, and skin conductivity. Galvanic skin response measures the conductivity of the skin; it has also been shown to indicate emotional state of a person and a person's sweat levels. Galvanic skin response may be measured using one or more electrodes in contact with skin. The heart-related metrics of the user may include, but are not limited to, metrics such as EKG or ECG, heart rate variability (HRV), heart rate intervals (RR), high frequency (HF) and low frequency (LF) of the RR, beats per minute, blood volume, blood pressure, cardiac rhythm, etc. The biometric sensor module 105 may be used for continual and/or periodic passive measurements of various biomarkers of a user. In some embodiments, the biometric sensor module 105 may be generic and may include both biometric sensors and non-biometric sensors (e.g. an ambient light sensor). In an embodiment, the biometric sensor module 105 may be integrated as a unit within the apparatus 100. In another embodiment, the biometric sensor module 105 may be comprised of several components dispersed within and/or throughout the apparatus 100.

The biometric sensor module 105 may include a temperature sensor and a biometric pulse sensor, such as the Pulse Rate Sensor from Karlsson Robotics. The temperature sensor may be used to measure the temperature of the user's skin at the location of the wearable apparatus 100. Silicon Labs makes an integrated circuit chip that includes a pulse rate sensor as well as blood oximetry (oxygen saturation of the blood). However, while these types of systems may be advantageous in determining whether the system was currently being worn, just the temperature sensor may be employed in accordance with some aspects if a design goal is to preserve battery life. For example, oximetry sensors that employ a light emitting diode and sensor to measure the oxygen saturation and have a high current draw may be omitted.

The biometric sensor module 105 may also include a device 107 for measuring the power exerted by a body part of the user by means of measuring a change in length over time of an elastic member, such as a strain gauge, a spring, a piezoelectric strain gauge, or an elastic band. The device 107 can be a generally cylindrical elastic member conforming to the shape of the body part on which it is worn, thereby remaining in constant contact with the body part's circumference. The device 107 would therefore generally be worn on a body part that is generally cylindrical, such as a forearm, wrist, finger, or forehead, and it can measure a contraction (decrease in size) or dilation (increase in size) of the object against time by measuring the change in length of the elastic member. This device 107 may therefore be used in conjunction with the motion sensor 104 to measure movements of the user wearing the apparatus 100, such as the flexing of muscles or prescribed motions. For example, the device 107 could be worn on the forearm as part of the apparatus 100, and measure the force of the user opening and closing the hand of the respective forearm. The device 107 could therefore contribute to active measurements of the user. Additionally, the device 107 can be used to identify the user based on the size and size change characteristics during a prescribed motion of the body part on which it is worn.

The biometric sensor module 105 may include sensors for measuring specific biomarkers, such as heart-related metrics of the user. The biometric sensor module 105 may therefore include a light emitting diode (LED) and a photodiode and/or photoreceptor in combination for detecting photoplethysmography (PPG) data on the user's blood volume. The biometric sensor module 105 may include an electrocardiograph.

Additionally, the device 107 for measuring the power exerted by a body part of the user by means of measuring the change in length of an elastic member, such as a strain gauge, spring, piezoelectric strain gauge, or elastic band, may be used to measure heart-related metrics of the user. The device 107 can be used to measure changes in diameter (contractions and dilations) of an enclosed cardiovascular system within the body part of the user (such as the radial artery within the forearm). This would therefore allow the device 107 to measure heart rate, cardiac rhythm, and blood pressure. The device 107 could also therefore contribute to the passive measurements of the user during monitoring.

The biometric sensor module 105 may also include one or more electrodes for contacting the skin of a user. The one or more electrodes may be configured to measure skin resistivity, skin conductivity, galvanic skin response, and electrodermal activity.

The biometric sensor module 105 may also be used to detect changes over time in the user's various biomarkers, including heart-related metrics and skin temperature. The changes may be detected through continual and periodic passive objective measurements of the user with the one or more sensors within the biometric sensor module 105.

In accordance with aspects of the invention, the wearable apparatus 100 is embodied in a comfortable wrist band, similar to a watch. However, the system could also work attached to the forearm, worn around the elbow, or attached to essentially any body part. Additionally, the apparatus may be incorporated into an article of clothing such as a glove or other means of holding it on the user. The design of the system in accordance with aspects of the system is such that it is not obtrusive for an operator to wear, helping to ensure that the operator wears it. Towards that end, the biometric sensor module 105 may be used to detect whether the wearable apparatus 100 is currently being worn (e.g., based on a temperature measurement indicating it is currently against the user's skin). For example, temperature sensors, pulse detection sensors, and/or biometric electrical impulse sensors would all work for this purpose. Other biometric sensors of the biometric sensor module 105 may be used for this purpose. Other examples of suitable sensors include, but are not limited to, capacitive touch sensors and proximity sensors. The motion sensor 104 and any monitored prescribed motions can also be used to determine whether the user is currently wearing the apparatus 100. If removed, the system may immediately alert the operator, instructing him to reattach the device, and if connected to a telematics system, may alert the dispatcher to inform them that the operator has removed the monitoring system.

A processor 108 is coupled to the motion sensor 104, the biometric sensor module 105, and generator(s) 106. The processor 102 may be a programmable microprocessor. The processor 108 is also coupled to a memory 110 for storing and retrieving data. The processor 108 may execute instructions stored in memory 110 to provide the functionality of the wearable apparatus 100 described herein. The processor 108 may also store data retrieved from the motion sensor 104 and biometric sensor module 105 in memory 110 and retrieve stored data from the memory 110 for processing. The memory 110 may be conventional memory such as, for example, static random access memory (RAM). The processor 108 may be a conventional microprocessor such as a low power consumption embedded processor. A reprogrammable microprocessor device may be employed, which enables firmware upgrades. A suitable processor 108 is an Altera MAX7000A, which operates at 3.3V (an operating voltage range compatible with suitable gyroscopes).

Processor 108 may also be coupled to a clock 112 for monitoring timed events and a transceiver 114 for transmitting signals to and/or receiving signals from a remote location. The clock 112 may be an integrated circuit clock capable of measuring time (e.g., in fractions of a second such as milliseconds, microseconds, etc.). The transceiver 114 may be, for example, a Bluetooth transmitter, e.g., to enable the wearable apparatus 100 to notify a telematics device, remote computer system, computer application, and/or a smart phone application in the event of a notification. The components of the wearable apparatus 100 may be powered by a battery 116. Battery 116 may be a rechargeable battery such as a lithium ion battery cell.

Processor 108 may monitor the temperature and motion outputs from the motion sensor 104 and the biometric sensor module 105 to determine whether the device is being worn against the skin. The motion outputs from the motion sensor 104 may be used by the processor 108 to monitor the motion of the wearable apparatus 100. The processor 108 may be configured to look for angular motion whose radius of motion is between 1-centimeter and 200-centimeters. The low end of the range eliminates small angular shifts due to vibration and the high end of the range eliminates large scale radial motion, such as from a turning truck. The clock 112, which measures time, allows for both the determination of the expiration of a main monitoring cycle, as well as the measuring of the operator's response time. The operator's response times as well as recorded temperatures and times may be stored in memory 110 so that, for example, a dispatcher can verify at a later point in time that the device was being properly worn in the event that a telematic system is not available to communicate.

Figure 1B:
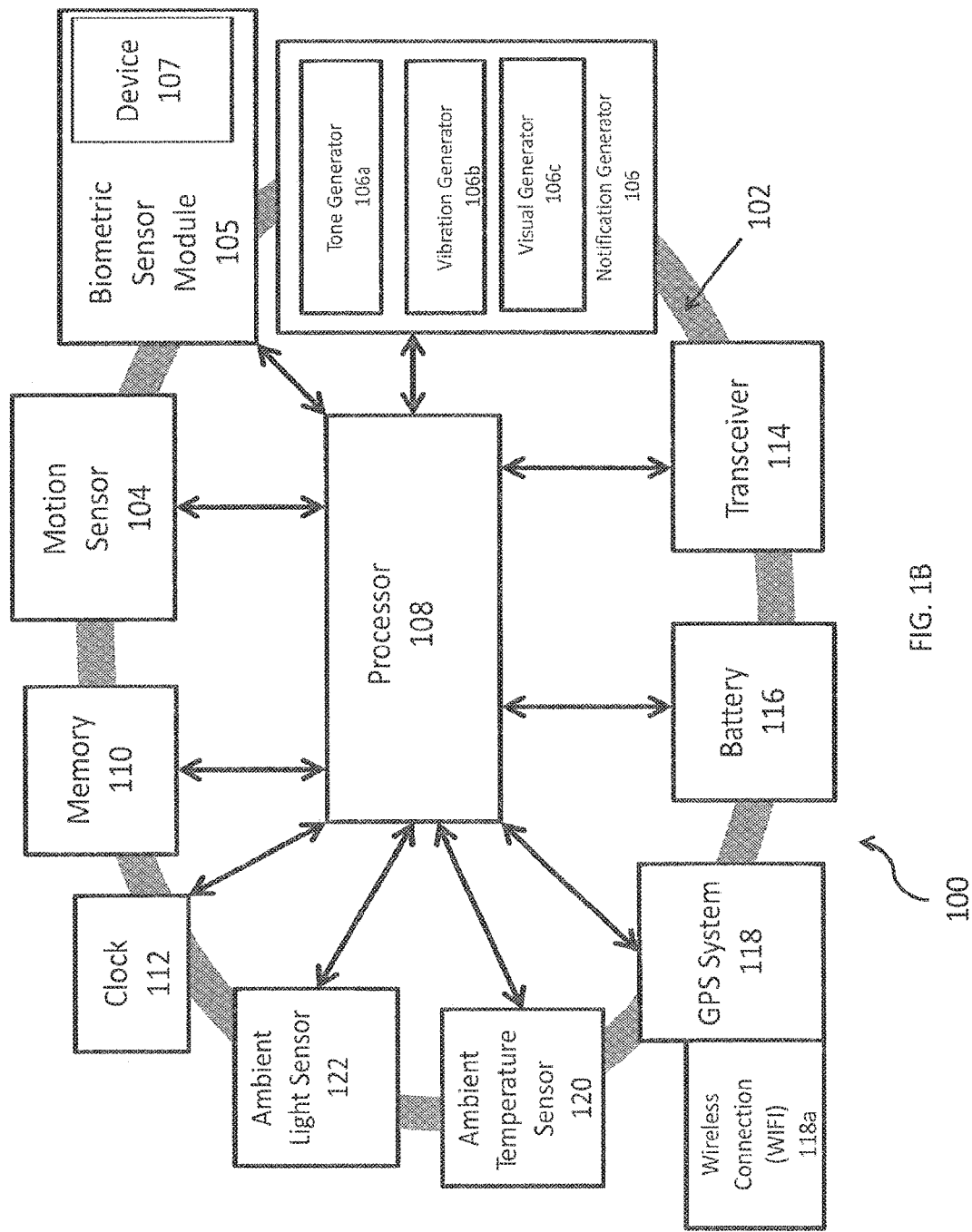

FIG. 1B depicts the wearable apparatus 100 operating in accordance with aspects of the invention for monitoring alertness and providing a notification to the user wearing the apparatus 100. The illustrated wearable apparatus 100 is embodied in a band 102, which may be placed on the user's wrist, for example. The band 102 supports at least one motion sensor 104 and a biometric sensor module 105 for monitoring the user and at least one notification generator 106 (e.g., tone generator 106a, vibration generator 106b, and visual generator 106c) for providing notifications to an entity, e.g., reminders and/or alerts (such as warnings and/or alarms). The tone generator 106a may be an audio tone generator and the vibration generator 106b may be an offset weight spinner. Suitable motion sensors 104, biometric sensor modules 105, and generators 106 for use with the present invention will be understood by one of skill in the art from the description herein.

Apparatus 100 may also include a GPS system 118 with an associated wireless connection (WIFI) 118a to track the location of the user wearing apparatus 100. The user's location could be sent via the WIFI 118a to a third party, to help monitor the personal security of the user or identify whether the user is on-task. The third party could use the location information to compare to an expected position or route for the user and provide an alert or notification to the user in the event of a deviation. In the event of an emergency, the third party could also provide emergency services personnel with the location of the user.

Apparatus 100 may also include an ambient temperature detector 120 for detecting the temperature of the user's environment. This could be used to improve the accuracy of any skin temperature measurements taken by a skin temperature sensor. The ambient temperature detector 120 could be placed on the apparatus 100 such that it has no contact with the skin of the user, and its measurements could be used to adjust the skin temperature data.

Apparatus 100 additionally could include an ambient light detector 122. The ambient light detector 122 could be used to detect the user's exposure to light. The ambient light detector 122 additionally could be specially designed to determine the user's exposure to blue wavelengths of light.

A processor 108 is coupled to the motion sensor 104, the biometric sensor module 105, and generator(s) 106. The processor 108 may also be coupled to one or more of the GPS system 118, the ambient temperature detector 120, and the ambient light detector 122.

Processor 108 may monitor and process the outputs measured by the motion sensor 104, the biometric sensor module 105, the GPS system 118, the ambient temperature detector 120, and the ambient light detector 122. The outputs may include sleep risk variables, which are applicable factors in determining a user's risk of falling asleep or risk of fatigue. The processor 108 may monitor and process sleep risk variables such as motion outputs measured by the motion sensor 104, biomarker outputs (i.e. biometric indicators) from the biometric sensor module 105, a location of the user within the user's personal circadian rhythm, subjective alertness levels input by the user, sleep drive of the user, current responsiveness profiles for the responses of the user to each stimulus, data derived from a chronotype input of the user, movements caused by the user, and the body position of the user. There may also be other sleep risk variables monitored and processed by the processor 108.

The biomarker outputs from the biometric sensor module 105 may be used by the processor 108 to determine whether the apparatus is being worn against the skin. In one embodiment, a capacitive touch sensor, which may be included in the biometric sensor module 105, can be mounted such that it touches the skin when the apparatus is worn. The capacitive touch sensor may indicate to the processor 108 whether the apparatus 100 is being worn.

The processor 108 may also be used to generate base responsiveness profiles of a user for prescribed motions. An example of how this occurs may begin with a user wearing the wearable apparatus 100 at a location on the user's body, such as a wrist, during an initial testing period. The user will typically be at rest during the testing period, i.e. not engaging in an activity that would imperil the user should the user become fatigued or desire to sleep. The user then performs a prescribed motion during the testing period. Initial measurements of the prescribed motion are taken, and the various parameters from these initial measurements may be used by the processor 108 to generate a baseline average and standard deviation for the parameters of the prescribed motion. These represent a base responsiveness profile for the parameters of the prescribed motion. Deviations from the base responsiveness profile can be used by the processor 108 to represent decreases in levels of alertness and increases in levels of risk.

Processor 108 may also establish a predetermined threshold for user responsiveness based on the generated base responsiveness profile. For example, the threshold could be two standard deviations from the base responsiveness profile average of the parameters of the prescribed motion. Since different users may have different base responsiveness profiles, the processor 108 may calculate an appropriate stimulus interval for alerting the user to perform the prescribed motion based on the generated base responsiveness profile for a specific user.

The processor 108 may also generate and send a signal to a notification generator 106 to issue an alert stimulus to perform a prescribed motion or warning to the user. When the user responds to the stimulus by performing the prescribed motion, the processor 108 may also generate a current responsiveness profile for the response by using the measured parameters of the prescribed motion. The processor may generate a current responsiveness profile for each response the user makes to each stimulus. The processor 108 may also store one or more current responsiveness profiles as one or more historical responsiveness profiles within the memory 136. The processor 108 may then send a signal to the notification generator 106 to generate a warning to the user if a current or historical responsiveness profile for a response falls outside an established predetermined threshold for user responsiveness.

A generated warning indicates to the user that the user may be too fatigued or too at risk of falling asleep to continue with the activity in which the user is engaged. The warning may be used by the user to know when to sleep and whether a nap is advisable to ward off fatigue or to decrease the risk of falling asleep. Additionally, the processor 108 may generate a position on an alertness scale for helping the user make appropriate decisions on the user's ability to perform the user's task adequately, with or without an alarm. The apparatus 100 could display to the user the processor's 108 generated location on an alertness scale through colors (e.g. red for dangerously low levels of alertness, yellow for moderate levels of alertness, and green for high levels of alertness), or on a numerical scale (e.g. on a scale from 1 to 10, where 1 is a dangerously low level of alertness and 10 is extremely alert).

Processor 108 may also generate a baseline fatigue risk level of the user based on initially measured sleep risk variables. An example of how this occurs may begin with a user wearing the wearable apparatus 100 at a location on the user's body, such as a wrist, during an initial testing period (which may be a short setup period of hours or minutes, or a longer testing period of three or more days). The processor 108 may use sleep risk variables initially measured during the test period, such as prescribed motions of the user, biomarkers, or a location within an estimated personal circadian rhythm of the user, to determine the user's natural predisposition to fatigue. The processor 108 can use this predisposition to generate the user's baseline fatigue risk level for falling asleep.

The processor 108 may then be able to incorporate a generated baseline fatigue risk level into its calculation of an appropriate stimulus interval for alerting the user to perform a prescribed motion. Additionally, processor 108 may calculate an appropriate stimulus interval based on a combination of both the base responsiveness profile and the baseline fatigue risk level of the user.

The processor 108 may use generated current responsiveness profiles and historical responsiveness profiles to generate dynamic risk levels of the user falling asleep over time during use of the apparatus 100. Each dynamic risk level represents a current, updated risk based on the parameters of each prescribed motion the user makes in response to a stimulus. For example, the user may have a delayed reaction time in responding to the stimulus, and the response's current and/or historical responsiveness profiles would reflect a potential drop in alertness. As a result, the processor 108 would generate an updated, dynamic risk level that shows an increase in risk of fatigue or falling asleep. The dynamic risk levels generated from each current and/or historical responsiveness profile may change over time, and the processor 108 can use the generated dynamic risk levels to continually recalculate and adjust the stimulus intervals. For example, as dynamic risk levels change to indicate a higher risk, the processor can recalculate and adjust a previously established stimulus interval to provide more frequent stimuli to the user.

Additionally, the processor 108 may also use measurements of one or more sleep risk variables to generate dynamic risk levels. The measurements are obtained by continually measuring the sleep risk variables after generating a baseline fatigue risk level. The apparatus 100 may detect changes over time in different sleep risk variables, and the processor 108 can incorporate these changes into calculations of updated dynamic risk levels. The processor 108 can then use these current dynamic risk levels to continually recalculate and adjust the stimulus intervals. For example, as changes in a sleep risk variable occur to indicate increasing fatigue risk of the user, new dynamic risk levels can be generated to reflect the increased risk.

General movements by the user during use of the apparatus 100 can be measured by the motion sensor 104 and processed by the processor 108 to create dynamic risk levels and adjust stimulus levels. Also, the processor 108 may register and identify stretches of time during which no discernible movement by the user is detected by motion sensor 104. These identified stretches of time can also be used by the processor 108 to generate and send a signal to the notification generator 106, to either alert the user with a stimulus or provide an alarm to the user.

The motion sensor 104 may detect general movements, which may then be processed by the processor 108, to determine a user's rest and/or waking cycles through actigraph techniques. Actigraphy is a non-invasive method of monitoring human rest/activity cycles involving measuring periods of movement and non-movement to predict whether or not a person (e.g. a user) is asleep or awake. Additionally the quality of sleep may be estimated based upon the amount of time between movements or with additional information from the biometric sensor module 105. Sleep time and quality may be estimated based upon information from the biometric sensor module 105 as well. For example, a decrease in heart rate or an increase in measured skin temperature may indicate that a user is asleep. The actigraphy and/or biometric sensor data on a user can be used by the processor 108 to generate baseline fatigue risk levels and/or dynamic risk levels.

The processor 108 can also use the sleep risk variable of body position of the user as measured by a motion sensor 104 to generate baseline fatigue risk levels and/or dynamic risk levels for the user. A user's body position (e.g. standing, sitting, lying down) is correlated with the user's level of alertness. For example, a user is likely to have a higher level of alertness if the user is standing rather than sitting or sleeping. The processor 108 can use the body position of the user to generate baseline fatigue risk levels and generate dynamic risk levels if the user's body position changes over time.

In one embodiment, a sleep risk variable includes one or more biomarkers. The biomarkers are correlated with a user's level of alertness and/or risk for fatigue and/or risk of falling asleep. For example, skin temperature has been shown to directly correlate with levels of alertness for a user. A large sudden increase in skin temperature at a distal body part of a user is directly associated with a decrease in levels of alertness for that user. The processor 108 can therefore monitor skin temperature as measured at a distal location on the user's body to determine the user's alertness. The processor 108 can also correct any measurements of skin temperature using measurements from an ambient temperature detector 120 to create a more accurate estimation of alertness based on skin temperature.

Another sleep risk variable that processor 108 might use to generate general and dynamic risk levels is a subjective alertness level input by a user of the apparatus 100. The subjective alertness level actively entered by the user may be incorporated by the processor 108 to adjust or offset estimated alertness levels. For example, a user of apparatus 100 may input the user's subjective estimation of the user's current level of alertness at any point during the user's use of the apparatus 100. The processor 108 can then use the user's subjective alertness input in generating an adjusted baseline fatigue risk level or dynamic risk levels over time. The subjective alertness of the user may be input into the apparatus 100 using verbal or text indications, a number representation, or a pictorial representation of an alertness or fatigue level. A user may enter the subjective alertness levels on the apparatus 100 itself, or via a remote application such as a smart phone or personal computer. Preferably, the user would not be able to adjust any generated baseline fatigue risk levels or dynamic risk levels to reflect an increase in alertness so as to increase any calculated stimulus intervals.

The processor 108 may use subjective input by the user to generate baseline fatigue risk levels and dynamic risk levels. The subjective input by the user may include information about when the user last slept and the duration of the last sleep period. This may be useful in situations where the user has not worn the apparatus within the preceding 24 hour period, as the apparatus 100 would not have been able to gather data from either the motion sensor(s) 104 or the biometric sensor module 105 to determine sleep time or duration through passive measurements. The subjective input may also include the user's estimation of the user's current fatigue. For example, the user may select a number on a number scale or a visual representation on the apparatus 100 of how fatigued the user feels. A visual representation may include a graphical scale of, for example, cartoon "faces" depicting various levels of fatigue from which the user may choose to represent the user's current estimated fatigue level.

The processor 108 may also incorporate the sleep risk variable of data derived from a chronotype input of a user to generate general and dynamic sleep risk levels. The user would preferably answer a set of questions regarding the user's lifestyle habits and general health risks prior to use of the apparatus 100. Based on the user's answers, a chronotype for the user could be generated. A person's chronotype indicates the person's propensity to sleep during a particular time within a 24-hour period. The chronotype would indicate if the person tends to stay up late at night or get up early in the morning, and indicates a person's sleep and wakefulness habits. Data derived from the chronotype can then be entered into the apparatus 100 for use by the processor 108. The data can then be used by the processor 108 to generate baseline fatigue risk levels and dynamic risk levels for the user during use of the apparatus 100.

Processor 108 may also generate responsiveness trend lines of the user from parameters of a prescribed motion using historical responsiveness profiles for each response of the user to the stimuli. Over time, a number of historical responsiveness profiles can be used by the processor 108 as points on a trend line for responsiveness. This can be used by the processor 108 to establish a threshold for deviation from the trend line. A measured response by the user to a stimulus which exceeds this threshold could be identified by the processor 108 during its generation of the current or historical responsiveness profile for the response. If the processor 108 determines that a current response deviates from the trend line such that it exceeds the threshold, the processor can generate and send a signal to the notification generator 106.

The processor 108 may process initial and continual/periodic measurements from the motion sensor 104 and biometric sensor module 105 to determine a sleep drive or propensity of a user. The sleep drive of the user may be composed of factors such as time since the user last slept (sleep debt), the length of the last sleeping session of the user, and the quality of the sleep during the last sleeping session of the user. Actigraphy data derived from the motion sensor 104 may be used by the processor 108 to obtain information about the user's sleep and wakefulness cycles. As the sleep drive of a user increases, the user's alertness tends to decrease. The detection of time sleeping and time since the user last slept can be determined by the processor 108 through analysis of biomarkers such as heart rate and skin temperature, combined with actigraphy movement data indicating the user's lack of movement (which would indicate time during sleep). Other biomarkers may be used as well. The initial measurements from the sensor 104 and module 105 can be used to determine these factors and calculate an overall sleep drive for the user. An initial sleep drive can be determined, and the processor 108 can update the sleep drive accordingly over time to adjust for changes to the factors (such as increase in the time since last slept, etc.).

The processor 108 may determine quality of sleep and duration of sleep by determining which sleep stages a person is in for different periods of time. The sleep stages may be determined based upon movement as measured by the motion sensor 104 through actigraphy techniques. The sleep stages may be determined based upon measurements of biomarkers taken by the biometric sensor module 105. These biomarkers may include, but are not limited to, heart rate or skin temperature data. The sleep stages that may be determined may include stages 1 through 3. Stage 1 sleep may be considered a "light sleep" where the user may be drifting in and out of sleep and may be awakened easily. In stage 2 sleep, eye movement may stop, and brain waves may become slower. In stage 3 sleep, the brain waves may slow down significantly, and it may be very difficult to wake a person experiencing stage 3 sleep. Stage 3 sleep may be referred to as "deep sleep." Additionally, stages of REM (Rapid Eye Movement) and non-REM sleep may be identified by detecting variations in biometric or motion sensors.

The processor 108 may process initial measurements of at least one biomarker to estimate the user's personal circadian rhythm. Research has shown that a user's alertness throughout the day can be strongly correlated with the position of a user within the user's circadian rhythm. The ability to estimate a user's circadian rhythm can provide an accurate prediction of the user's alertness at any point in a given day.

A biomarker for estimating a user's personal circadian rhythm is the user's distal skin temperature. A user's distal skin temperature is correlated with the user's core body temperature. The core body temperature follows the user's circadian rhythm, and the core body temperature will increase during the hours of wakefulness and decrease during typical sleeping hours as a result of following the user's circadian rhythm. The user's levels of alertness will therefore also change with the circadian rhythm. Because the user's body regulates core body temperature by dissipating heat through the limbs of the body, the temperature of the limbs increases when core body heat decreases. Therefore, the measurements of a user's distal skin temperature can be used to accurately estimate the user's personal circadian rhythm by correlating the distal skin temperature with core body temperature, which follows the circadian rhythm of the user. This provides a model of alertness levels for the user.

Distal skin temperature may also be correlated with a user's melatonin levels. A user's level of endogenous melatonin is a reliable and accurate indicator of the user's location within the personal circadian rhythm and therefore an indicator of the user's degree of alertness. Melatonin typically rises during times of decreased alertness (e.g., the period before nightly sleep) and typically falls during times of increased alertness. Skin temperature generally correlates with melatonin levels in that when melatonin levels increase, the skin temperature of the user also increases in connection with the user's circadian rhythm. In this way, skin temperature may act as a correlative proxy for determining the user's current levels of melatonin, and therefore the user's current levels of alertness as determined by the user's location within the personal circadian rhythm.

Initial measurements of a person's distal skin temperature for estimation of a user's personal circadian rhythm and/or melatonin levels may be taken at various locations on the user's body, including feet, arms, wrists, and hands. Other initial measurements of biomarkers that may be incorporated into the processor's 108 estimation of a user's personal circadian rhythm and/or melatonin level may include, but are not limited to, heart-related metrics.

Figure 2:
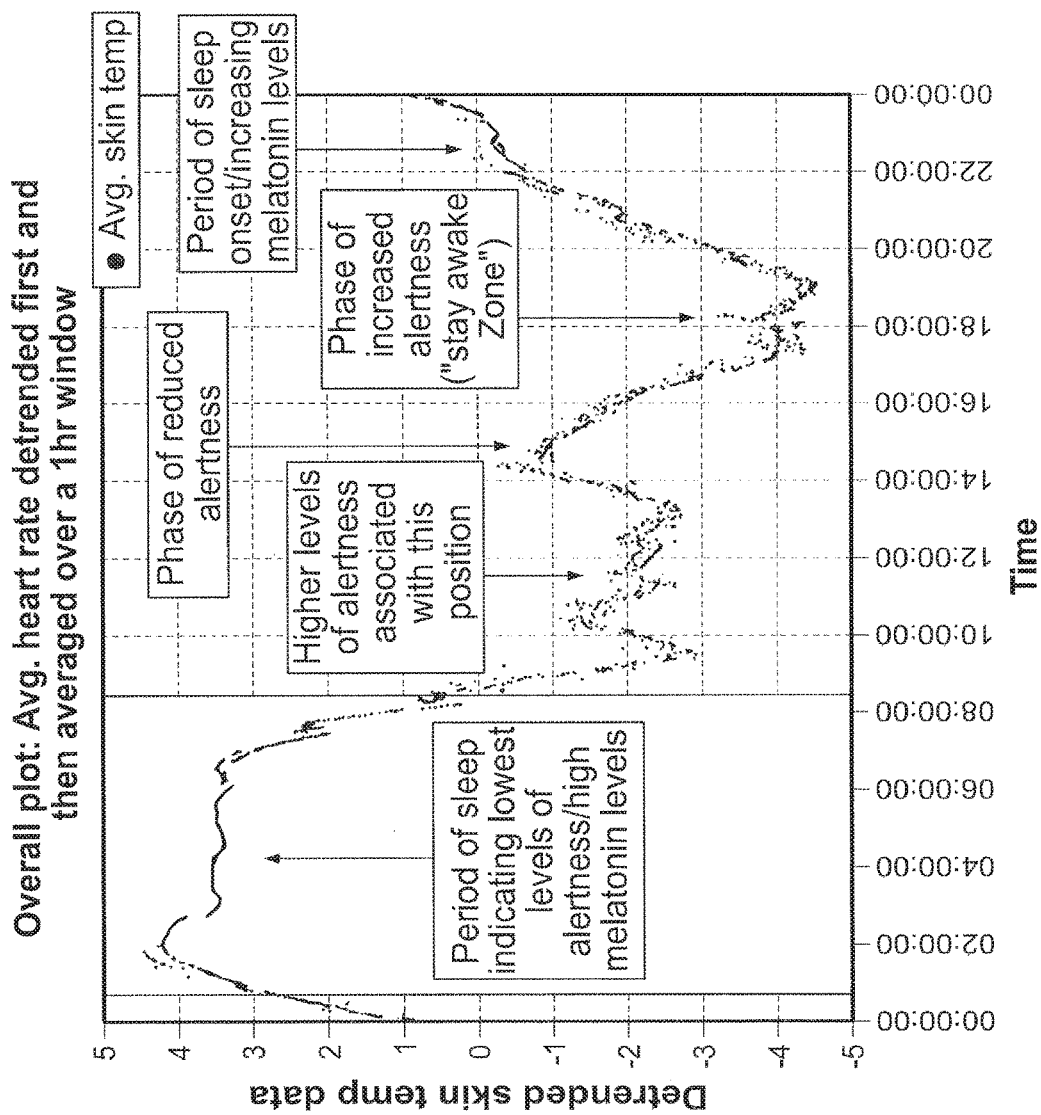
FIG. 2 is a chart depicting measurements of a user's ambulatory skin temperature in relation to the user's circadian rhythm measurements of the user's ambulatory skin temperature are taken over the course of seven days measurements of the user's ambulatory skin temperature are taken over the course of seven days.

An example of estimating a user's personal circadian rhythm may begin with the user wearing the wearable apparatus 100 at a distal location on the body, such as the wrist, for a testing period. The testing period may have a duration of three or more days. The user will typically be at rest, i.e. not engaging in an activity that would be imperiled should the user become fatigued or desire to sleep. Initial measurements are taken of certain sleep risk variables, including biomarkers such as skin temperature, such that sufficient data is collected to estimate the user's typical circadian rhythm. Ambulatory skin temperatures may be measured by the biometric sensors 104b at a frequency of once per minute for the span of the at least three days. In one example, measurements of the user's ambulatory skin temperature are taken over the course of seven days from the user's wrist (FIG. 2). Based on the data derived from the distal skin temperature measurements, the processor 108 may estimate a user's personal circadian rhythm. Other initial measurements of biomarkers over the testing period may also be used to estimate the circadian rhythm of a user.

Changes in body position and/or activity of a user may "mask" phases of the user's personal circadian rhythm. As a result, the processor 108 can be programmed to remove these "masking events" from the estimation of the user's personal circadian rhythm. This "removal" process can include scaling the circadian rhythm data the processor 108 receives to correct for body position as measured by the motion sensor 104a, and then averaging the data over the course of a testing period. The processor 108 can also scale the circadian rhythm data it receives to correct for any activity of the user during the testing period, as measured by the sensors 104. The "corrected" data can then be used by the processor 108 to create a more accurate estimate of the user's personal circadian rhythm.

The processor 108 may also monitor where a user is located within the user's personal circadian rhythm at a given point in time, based on a personal circadian rhythm estimated by the processor 108 for the user. The location of a user within the user's circadian rhythm may be used to determine baseline fatigue risk levels and/or dynamic risk levels, since the location within the circadian rhythm is correlated to a user's reaction times and subjective alertness levels. The processor 108 may compare the estimated circadian rhythm to other processed initial measurements, such as parameters of the prescribed motion acquired during the testing period, to verify a correlation between alertness due to location within the circadian rhythm and responses of the user performing the prescribe motion.

FIG. 2 depicts a graph having detrended ("demasked") skin temperature data showing the average distal skin temperature of a user during a 24-hour period, averaged from a seven-day period of observation. A person's circadian rhythm is typically phasic about a 24-hour period. The periods of higher distal skin temperature correlate to higher levels of melatonin and decreased levels of alertness within the individual's personal circadian rhythm, indicating a phase of fatigue. The periods of lower distal skin temperature correlate to increased levels of alertness within the individual's personal circadian rhythm, indicating a phase of alertness. For example, a circadian rhythm may indicate a phase of increased alertness in the mid-morning hours, followed by a roughly two-hour phase of reduced alertness between the hours of 2 pm to 4 pm. This may be followed by a phase of increased alertness from between 6 pm to 8 pm, which may be designated as a "stay awake zone." This "stay awake zone" may then be followed by a sharp decline in alertness and increase in temperature and melatonin in preparation for sleep. Phases depicting potential for higher risk of fatigue and higher propensity for alertness are labeled on FIG. 2.

The processor 108 may incorporate the location of a user within the user's personal circadian rhythm into the generation of the baseline fatigue risk level for that user falling asleep. For example, the processor 108 can incorporate the location of the user within the user's personal circadian rhythm and/or the user's determined sleep drive to create a cumulative estimated baseline fatigue risk level. Also, the processor may incorporate changes over time in the user's location within the circadian rhythm to generate dynamic risk levels to reflect changes in risk at different locations in the circadian rhythm.

Exposure to light may affect a user's personal circadian rhythm, e.g., exposure to blue light wavelengths. Light exposure can cause a "phase shift" effect on a user's circadian rhythm. The direction of the "phase shift" in the circadian rhythm depends on which location in the circadian rhythm a person is exposed to light. The processor 108 can use measurements taken by the ambient light sensor 122 and determine the effect of any light exposures on the user's personal circadian rhythm. In an embodiment, the ambient light sensor 122 may be located in the biometric sensor module 105. The ambient light sensor 122 may be located on the underside of the apparatus 100 and operate by detecting leakage of ambient light under the apparatus 100. In another embodiment, the ambient light sensor 122 may be separate from the biometric sensor module 105. The detected exposure to light can also be used to determine where a user is within the user's personal circadian rhythm. The processor 108 can use the detected light exposure to pre-process circadian rhythm data and produce a more accurate estimated personal circadian rhythm for a user, as well as a more accurate location of the user within the user's estimated personal circadian rhythm.

Figure 1C:
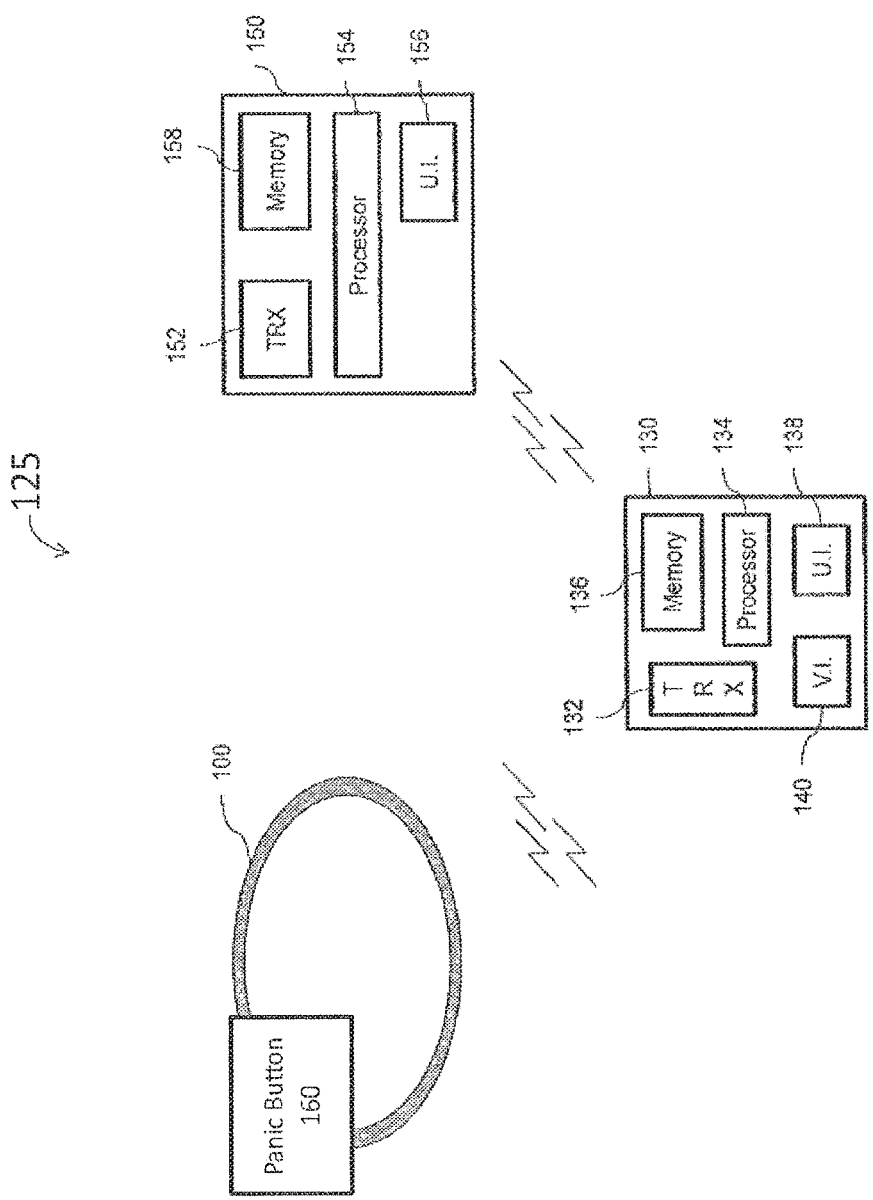
FIG. 1C is a block diagram of a system including the wearable apparatus of FIG. 1A or 1B, and a remote facility in accordance with aspects of the present invention.

FIG. 1C depicts a system 125 in which the wearable apparatus 100 may operate in accordance with aspects of the invention. It is to be understood that the wearable apparatus 100 may be utilized on its own without any other components such as those depicted in FIG. 1C.

The illustrated system 125 includes the wearable apparatus 100, a local remote device 130, and a non-local remote device 150. Wearable apparatus 100 may communicate with non-local remote device 150 through local remote device 130 in accordance with aspects of the invention. Alternatively, wearable apparatus 100 may communicate directly with non-local remote device 104, in which case local remote device 130 may be omitted. In yet alternative embodiments, wearable device may only need to communicate with local remote device 130, in which case non-local remote device 150 may be omitted. In another embodiment, the apparatus 100 may communicate with a "cloud" storage system, and may send data to the cloud for storage.

The local remote device 130 includes a transceiver 132 for communicating with the wearable apparatus 100 and optionally the non-local remote device 150. The local remote device 130 includes a processor 134 for controlling operation of the local remote device 130. The processor 134 is coupled to a memory 136 that may store instructions for execution by the processor 134 and for storing data from the processor 134 for later retrieval.

The local remote device 130 may include a user interface 138 for providing visual and/or audible notifications and/or instructions to the user. Additionally, the local remote device 130 may include a vehicle interface 140 (such as a wired or wireless interface, e.g., Bluetooth) for communicating with a vehicle, e.g., in order to use the vehicles sound system for notification. The local remote device 130 may be embodied in a mobile device such as a cellular phone.

The non-local remote device 150 includes a transceiver 152 for communicating with the local remote device 130 or directly with the wearable apparatus 100. The non-local remote device 150 includes a processor 154 for controlling operation of the non-local remote device 150. The processor 154 is coupled to a memory 158 that may store instructions for execution by the processor 154 and for storing data from the processor 154 for later retrieval.

The non-local remote device 150 may include a user interface 156 for providing visual and/or audible notifications and/or instructions to another party, e.g., an employer, teacher, parent of the user wearing the wearable apparatus 100.

Apparatus 100 may also include a "panic button" 160 for the user to press in an emergency, such as a medical issue or a situation with an intruder. The panic button 160 may be pressed, either once or in a prescribed pattern or motion, to inform a third party. The non-local remote device 150 may be at the same location as the third party. The third party may be a monitoring company (such as Torvec), a dispatch unit, or a 911 call center.

Figure 3:
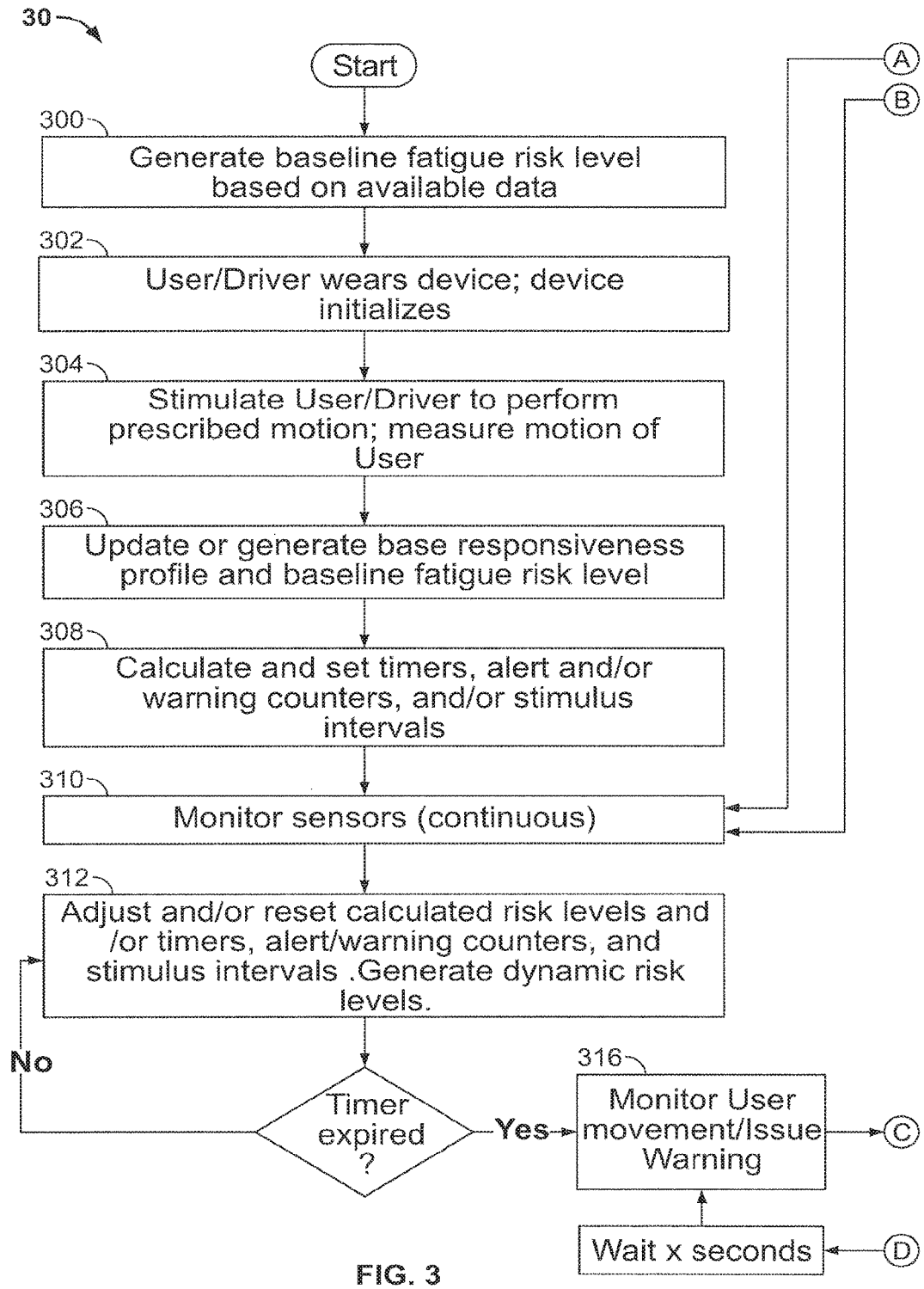
FIGS. 3 and 4 are flow charts of other steps for monitoring and alerting a user and/or others in accordance with aspects of the present invention.
Figure 3:
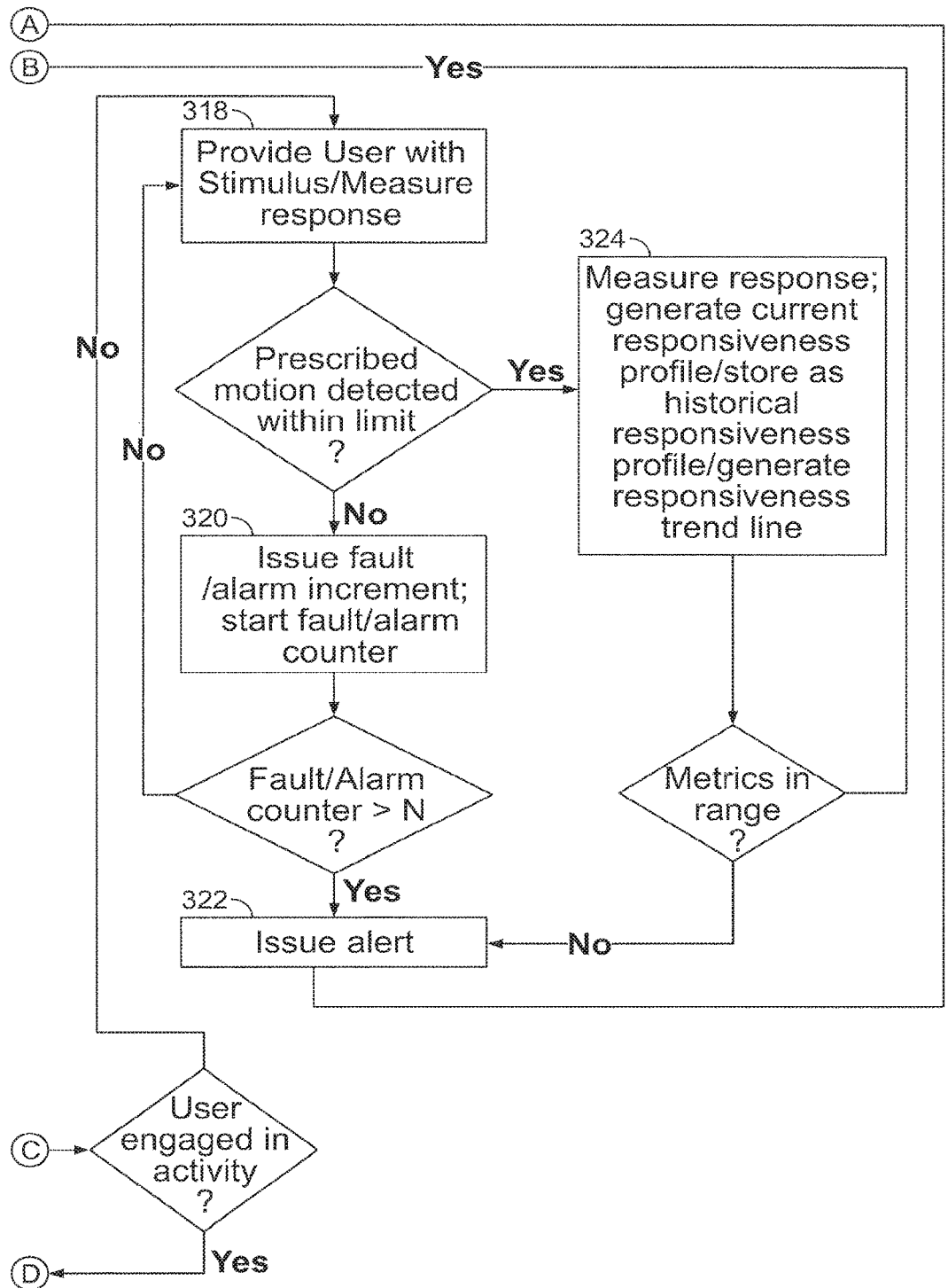

FIG. 3 depicts steps for monitoring an operator of a vehicle and notifying the operator and/or another entity.

As can be seen in the flow chart 30, the operating logic of the system is such that it may continuously monitor the wearer, i.e. the user, of the apparatus to check for motion and provides a warning if a lack of motion is detected. If the system does not receive an acknowledgement in response to the warning, or if the system detects an overall degradation of alertness of the user after issuing a stimulus to perform a prescribed motion, the system then generates an alarm or fault. This alarm or fault notifies the user (and optionally others in the vicinity of the user) that the system has detected a decrease in alertness. It can also include external notifications, such as alerting a third party, e.g. a dispatcher, after a predetermined number of faults, through a connection to a telematics device or through email, recorded voice message, or texting through an external phone or smart device, and/or can include additional notification and alert responses such as turning on the a vehicle's hazard flashers and/or disengaging any cruise control through a connection to the vehicle, if the user is operating a road vehicle such as a truck. For aircraft, it could engage an auto-pilot to maintain the current course and altitude if one is not already engaged.

First, at step 300, a baseline fatigue risk level for the user may be generated based on any available data. Available data may include health information of the user, subjective alertness levels input by the user into the apparatus prior to wearing it or while wearing the apparatus, a sleep history input by the user into the apparatus about the duration of last sleep and the length of time elapsed since waking. In one example, the baseline fatigue risk level may be determined from data gathered in a controlled environment (e.g., a laboratory), and additional information may be gathered (e.g., age, sex, drug test results). In another example, the baseline fatigue risk may be determined in an uncontrolled environment (e.g., vehicle operator generates baseline fatigue risk in vehicle without supervision prior to operating the vehicle). In another example, the base responsiveness profile may be determined in the controlled environment or uncontrolled environment while the baseline fatigue risk is being generated. The user may be prompted at step 300 to perform an action, after which the user's base response is captured and a base responsiveness profile is generated. The base responsiveness profile and baseline fatigue risk level may be determined periodically at set or random intervals (e.g., every six months).

A baseline fatigue risk level of the user may also be generated based on initially measured sleep risk variables. An example of how this occurs may begin with a user wearing the wearable apparatus at a location on the user's body, such as a wrist, during an initial testing period (which may be a short setup period of hours or minutes, or a longer testing period of three or more days). Sleep risk variables initially measured during the test period may include prescribed motions of the user, biomarkers detected by the biometric sensor module, or a location within an estimated personal circadian rhythm of the user. The sleep risk variables can then be used to determine the user's natural predisposition to fatigue. This predisposition can then be used to determine the user's baseline fatigue risk level.

At step 302, the user may put the apparatus on. After the apparatus is first put on it powers up and performs its initialization sequence. This could occur through such means as a manual on switch, detecting the micro-currents from contact with the skin (i.e. capacitive touch), a contact switch in the band such that when clasped, the switch engages, or any other of a number of similar means. Alternatively, the initialization sequence and the time when the user is monitored may be dynamic based upon the apparatus/device detecting a driving event, a schedule input by the wearer or a third party, or manual initialization by the wearer or a third party. A driving event may be detected using acceleration measurements from a motion sensor or location information from a GPS unit. Acceleration measurements and location information may also be used to determine when the driving event has stopped and whether the wearer should be actively monitored. The device/apparatus may also be used to monitor motion of the vehicle by measuring the frequency of road vibrations, the acceleration information, and the location information. This could help the wearer or a third party monitor the wearer's driving behavior, such as driving speed, rate of braking, etc.

After initialization is complete, the system may initiate a stimulus at step 304 (e.g., a vibration) in order to prompt the wearer to perform a prescribed action. The apparatus may then capture the user's base response, generate a base responsiveness profile (if not generated previously or as an update to a previously generated base responsiveness profile) at step 306, and ensure that the user can detect the stimulus.

At step 308, alert/warning counters, stimulus intervals, and timers are calculated and set to their starting values. The count-down timer for the primary motion monitoring loop is initialized and started. A generated baseline fatigue risk level may be incorporated into the calculation of a count-down timer and an appropriate stimulus interval for alerting the user to perform a prescribed motion. Additionally, an appropriate stimulus interval may be calculated based on a combination of both the base responsiveness profile and the baseline fatigue risk level of the user.

At step 310, the primary motion monitoring loop begins, and motion of the user is continuously monitored while the timer remains counting down. Inside the primary motion monitoring loop, the device is monitoring the signals from the motion sensors indicating general movement of the user (passive measurements of motion). If any appropriate motion is detected during the count-down, the timer for the primary motion monitoring loop may be reset (see step 312) and the loop begins again. Appropriate motion in the primary loop is any motion that is distinguishable as motion of the user and not the vehicle; for instance, turning the steering wheel or the pilot's yoke; reaching out to adjust a dial, knob, or other device in the cabin or cockpit; raising a cup to drink; scratching an itch; shaking the wrist; or any other motion that generally has an angular component whose radius of motion is too small for the vehicle to make. In one embodiment, the motion of the wearer/user may be distinguished by a radius of motion greater than or equal to 1-centimeter and less than or equal to 200-centimeters (e.g., a radius between 1 centimeter and 200 centimeters). Step 310 may also include continuous monitoring of various sleep risk variables, including biomarker signals received from the biometric sensor module (passive biometric measurements). Signals from both the motion sensor(s) and/or the biometric sensor module may be continually monitored during the time that the user is wearing the apparatus.

Continuous and/or periodic measurements of one or more sleep risk variables may be used to generate dynamic risk levels for user fatigue at step 312. The measurements may be obtained by continually measuring the user's sleep risk variables (including biomarkers) after generating a baseline fatigue risk level and/or base responsiveness profile. Changes over time in different sleep risk variables may be incorporated into calculations of dynamic risk levels. These current dynamic risk levels may then be used to continually recalculate and adjust the stimulus intervals and/or countdown timers at step 312. For example, as changes in a sleep risk variable occur to indicate increasing fatigue risk of the user, new dynamic risk levels can be generated to reflect the increased risk.

Additionally, general movements by the user may be continuously and/or periodically measured and processed to aid in creating dynamic risk levels and also can be used to further adjust stimulus levels at step 312. At the same time in the primary loop, the timer continues to count down. If the timer ever reaches zero, the user is monitored for any motion for a given amount of time. Should the time pass without the user engaging in activity, a stimulus to perform the prescribed movement may be issued (see step 318). This loop may be set to, for example, between 15-seconds and 45-seconds, depending on the operator, with a default value of 30-seconds. In the event the system starts to see a slight degradation of response time, this timer interval can be shortened.

Also, stretches of time during which there is no discernible movement by the user can be registered and identified. These identified stretches of time can also be used to issue a warning to the user to prepare for a stimulus at step 316 (which may also occur after a count-down timer has expired, as shown in the flow diagram). The warning may be issued to allow the user to get ready to respond to a stimulus. After a warning has issued due to lack of motion by the user for an extended period of time, a secondary loop starts wherein the user is monitored for any further activity and/or motion. If the motion and/or activity occurs, the apparatus waits a predetermined number of seconds (x seconds) and monitors the user again for motion at step 316. Should there be another lack of activity, the system may again issue a warning to the user and/or provide the user with a stimulus to make a prescribed motion at step 318. Additionally, the apparatus may communicate an alert to a third party (e.g., a dispatcher) and/or provide an alarm or fault to the user.

The stimulus applied to the user at step 318 may vary in intensity. A stimulus may start at a lower intensity and increase in magnitude (e.g. increase in sound and/or in strength of vibration) throughout the application of the stimulus. Depending on when the stimulus is perceived by the wearer, as determined from when an appropriate motion is detected in response to the stimulus, the alertness of a user may be further determined. For example, if a wearer/user detects and responds to a low-intensity stimulus soon after the stimulus is applied, that may indicate a higher level of alertness than if the wearer allows the stimulus to increase in intensity over time until such time the wearer responds appropriately.

Upon issuing a stimulus, the system may start a count-up timer. This measures the amount of time it takes for the wearer to perform a specific motion in response to the stimulus. The response to the stimulus may be a wrist shake by the wearer (i.e., manual). When that motion has been detected, the response time and other response parameters are then captured. If no motion has been detected within a preset amount of time, an alarm or fault is issued to the user and a fault/alarm counter is started to increment the number of faults or alarms issued to the user at step 320. In one embodiment, this preset amount of time is 5-seconds. In the event this occurs, an alarm or fault is issued (e.g., by the apparatus or another device in communication with the apparatus) and an alert counter is incremented. If the number of incremented faults or alarms is less than a predetermined number (N), another stimulus is given. If no motion is again detected, then the alarm may be escalated and any alerts, such as contacting central dispatch or turning on hazard lights, are sent at step 322. An alert may be issued when the number of incremented faults/alarms exceeds predetermined number N. A predetermined threshold for dynamic risk level may be determined. In an embodiment, a fault/alarm may be issued to the user based upon an updated dynamic risk level for fatigue that exceeds this threshold. In yet another embodiment, an alert may be issued to a third party based upon an updated dynamic risk level that exceeds the threshold. After the alert is issued, the system may continue to monitor sensors as depicted in step 310, and the cycle continues.

If the wearer does respond in an acceptable amount of time to the alarm response parameters are measured at step 324. A current responsiveness profile may be generated from the data of the parameters. Each current responsiveness profile may also be stored as a historical responsiveness profile. Parameters from a current responsiveness profile may be compared against the parameters of a historical responsiveness profile that has been stored. For example, the response time of a current responsiveness profile may be compared to previously stored response times of a historical responsiveness profile. A trend line based on historical responsiveness profiles may also be generated, along with a predetermined threshold for the trend line. Should the trend line, as plotted over time, exceed the threshold, it may indicate a significant degradation of the user's response parameters.

A current responsiveness profile may be compared against the base responsiveness profile at step 324. The overall base responsiveness profile may have an associated predetermined threshold, or a specific parameter may have a predetermined threshold and a corresponding specific deviation from the base responsiveness profile (e.g. two standard deviations from the base response of a certain parameter). If the current responsiveness profile deviates such that the predetermined threshold is exceeded, it may indicate a significant degradation of the user's response parameters.

If there is a significant degradation indicated by comparisons of current responsiveness profiles to historical responsiveness profiles and/or the base responsiveness profile, a fault or alarm may be provided (e.g., to the user) and/or an alert is issued to a third party indicating the user is starting to lose attentiveness and response time. If there is no degradation (i.e. the parameters are within a proper range), the system returns to the primary monitoring loop. If there is a slight degradation, the system may shorten the countdown timer value at step 312 (e.g., by 5 seconds) and/or contribute the data indicating the slight degradation to the generation of dynamic risk levels at step 312 for the primary monitoring loop prior to returning to it.

A "boredom drive" effect may occur when a user/driver has been operating a vehicle for an extended period of time on a relatively straight path. The driver in such a situation may enter a period of boredom, which translates into decreased movement and a corresponding decrease in alertness. As a result, the wearable apparatus/device may detect these periods of boredom via detecting decreased movements over lengthy, straight paths. As time between significant movements increases, the "boredom drive" of the driver can be estimated and incorporated into calculations which increase, for example, dynamic risk levels of the driver for fatigue (thereby contributing to an adjusted and decreased stimulus interval). The longer the time from the last significant movement of the driver, the higher the risk. Upon detection of a significant movement by the driver, the boredom drive may reset.

The wearable apparatus/device may also be used to detect movements that indicated drowsiness while the driver is driving. Movements that may indicate drowsiness include, but are not limited to, a sudden drop of the driver's arm or changes in the movement of the steering wheel. The motion sensor(s) 104 of the apparatus/device 100 may detect these movements, and the apparatus/device could increase, for example, a dynamic risk level and reduce the stimulus interval accordingly, and/or generate a warning to the driver that the driver should stop driving and rest. The device/apparatus could also provide to the driver an indication of the driver's location on an alertness scale.

Figure 4:
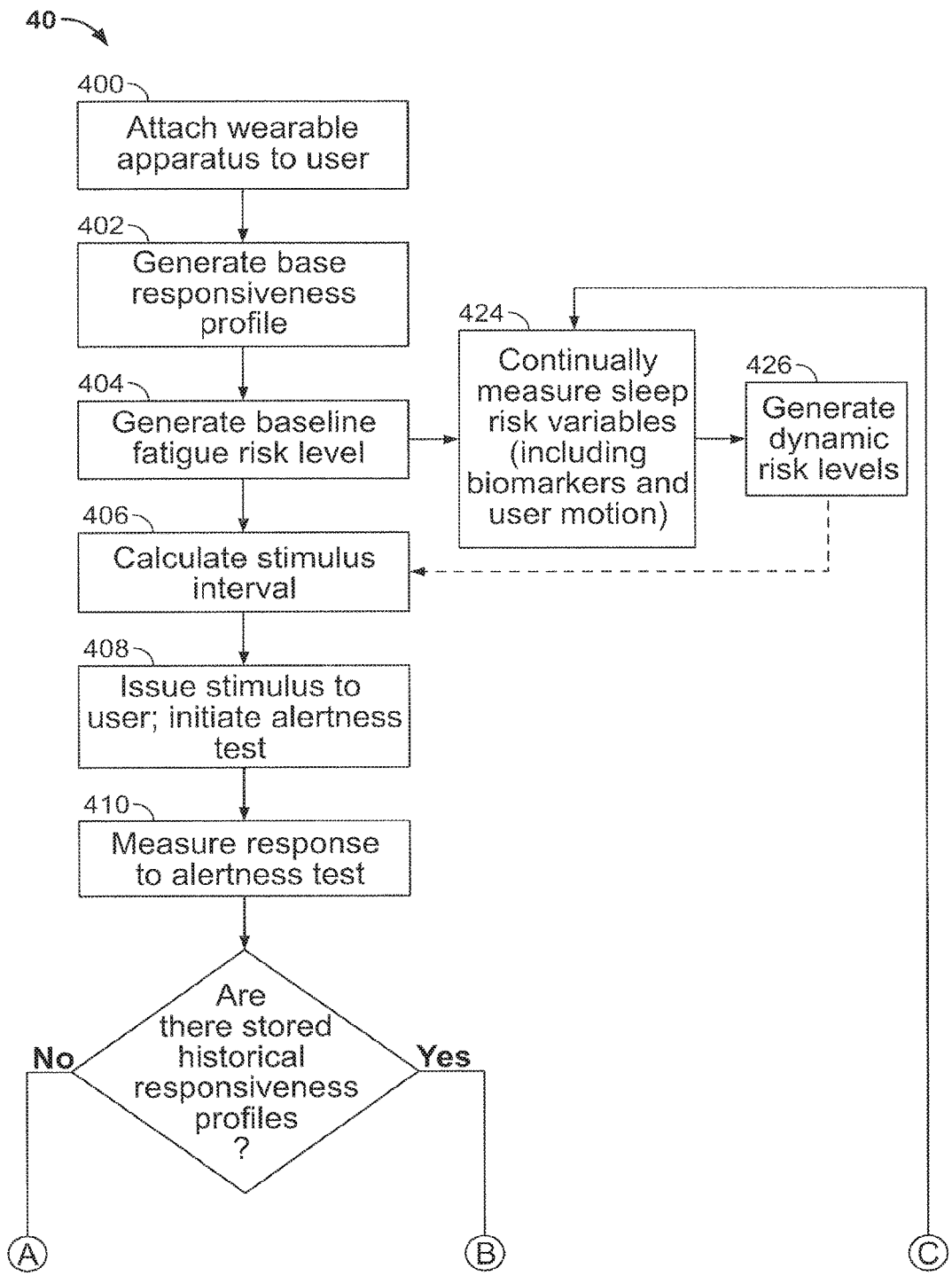
Figure 4:
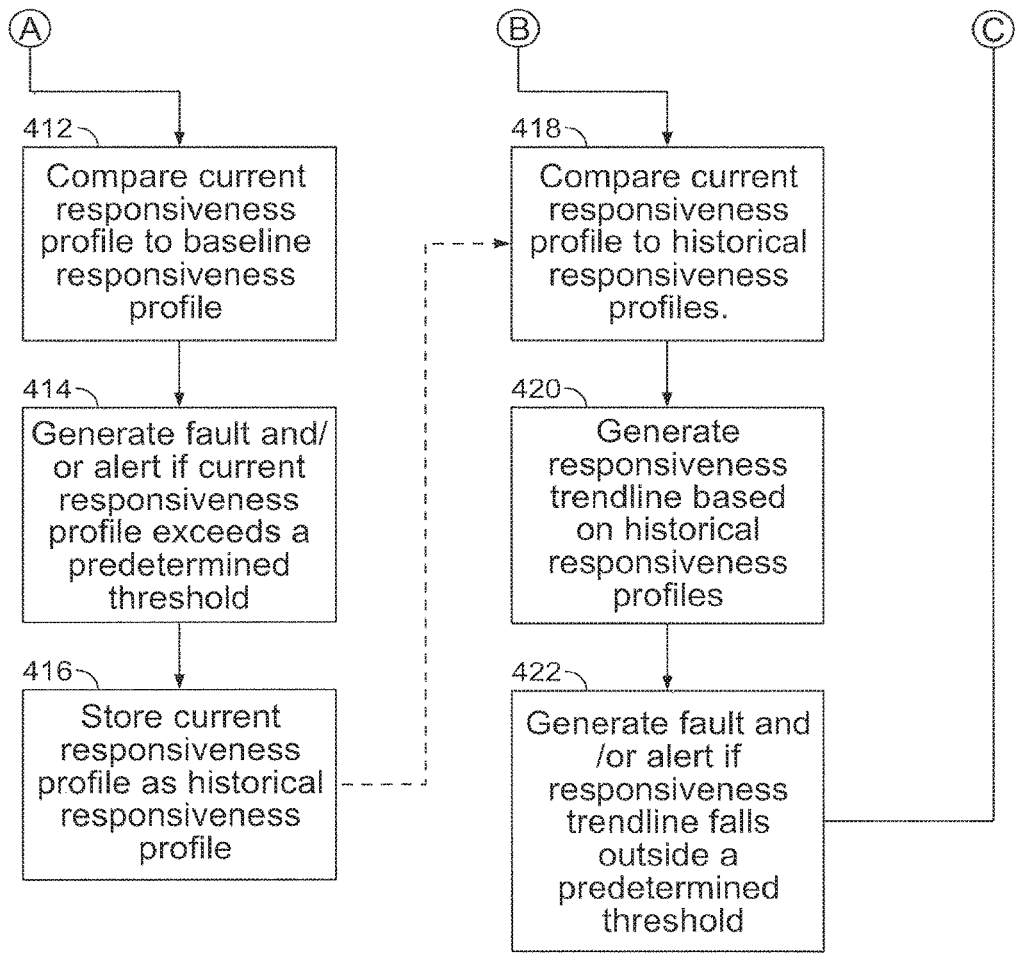

Referring next to FIG. 4, a flowchart 40 of steps for monitoring the alertness of a user are shown. At block 400, the user attaches a wearable apparatus to his or her body. The apparatus may be a wristband, similar to the wristbands described above with respect to FIGS. 1A, 1B, and 1C. In one embodiment, the wearable apparatus is self-contained, such that all functionality is conducted within the apparatus (e.g., electronics in the apparatus). In another embodiment, the wearable apparatus functions with and is in communication with an external device, such as a smart phone, mobile application, central server, etc.

At block 402, a base responsiveness profile for the user is generated. The base responsiveness profile may be generated when the wearable apparatus is placed in an initialization mode (e.g., activated when the apparatus is attached to the user, activated via a controller, activated from a software application, mobile device, central server, etc.). The base responsiveness profile functions as a baseline profile against which future active responses from the user are measured. In one example, the base responsiveness profile may be determined in a controlled environment (e.g., a laboratory) and additional information may be gathered (e.g., age, sex, drug test results). In another example, the base responsiveness profile may be determined in an uncontrolled environment (e.g., vehicle operator generates base responsiveness profile in vehicle without supervision). The base responsiveness profile may be determined periodically at set or random intervals (e.g., every six months).

The base responsiveness profile may be generated from one or more initial measurements of a prescribed motion of the wrist, arm, elbow, and/or other body parts of the user from which the wearable apparatus can detect movement. The base responsiveness profile may be generated from one or more performances of the prescribed motion by the user. Where multiple performances of the prescribed motion are performed, the responsiveness profile may be generated by averaging parameters obtained from the performances of the prescribed motion. Additionally, the prescribed motion used to generate the base responsiveness profile may be changed at set or random intervals (e.g., to prevent the prescribed motion from becoming routine and, therefore, potentially less effective at determining alertness). In one embodiment, two or more base responsiveness profiles may be generated from corresponding different prescribed motions.

In an embodiment, the prescribed motion is a particular rotation of the hand (and, by extension, the wrist and forearm). For example, the prescribed motion may require the user to rotate a hand attached to a wrist including the wearable device from a starting location a particular number of degrees in a first direction about at least one axis (e.g., a single axis extending between the user's elbow and wrist) and to reverse the rotation direction of the hand to return the hand to the starting location. The prescribed motion may require the user to rotate the hand from a particular position to between about 90 degrees (±5 degrees) and about 180 degrees of the particular position and back to the starting position. In an embodiment, the prescribed motion requires the user to rotate a hand between about 100 degrees and about 120 degrees and back to the starting position. In an embodiment, one prescribed motion may be with the hand open and another prescribed motion may be the same motion with the hand closed in a fist. It is noted that certain prescribed motions (or portions thereof) can be completed in a shorter period of time that other prescribed motions/portion (e.g., a user can generally to complete a pronation to supination motion with their hand faster than a supination to pronation motion). Such distinctions in motion can be used to select appropriate prescribed motions that are most effective in determining degradation of alertness.

Figure 6:
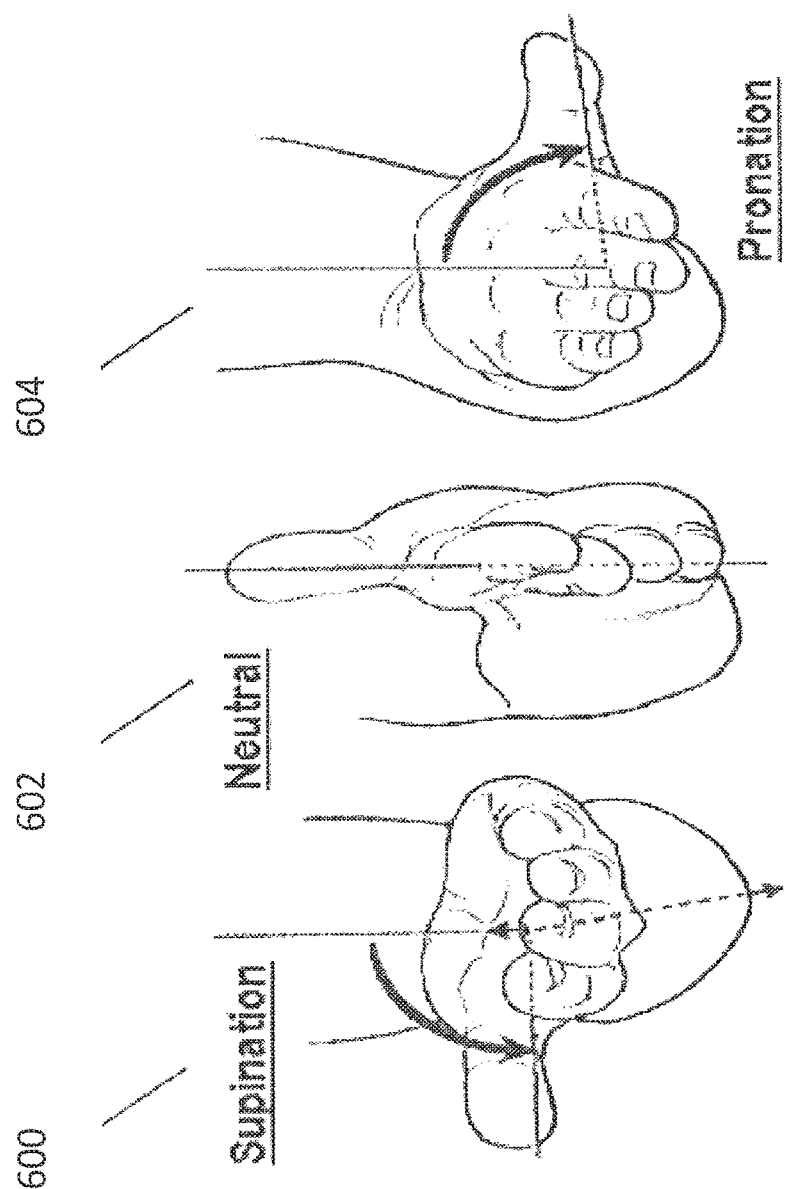
FIG. 6 depicts various hand, wrist and forearm positions for prescribed motions in accordance with aspects of the invention.

In embodiments where the prescribed motion requires rotation of the hand, it is advantageous that the rotation of the hand result in a change in acceleration detectable by sensors integrated to the wearable apparatus. The prescribed motion of the hand of a user may require rotation of the hand (along with the wrist and forearm) about at least one axis (e.g., a single axis extending along the forearm, between the wrist and the elbow). In one example, the user may be requested to start with his hand in approximately a supination position 600 (FIG. 6), rotate his hand (along with the wrist and forearm) past a neutral position 602 towards a pronation position 604, and return his hand to approximately the supination position 600. In another example, the user may be requested to start with his hand in approximately the pronation position 604, rotates the hand past the neutral position 602 toward the supination position 600, and return his hand to approximately the pronation position 604. In another example, the user may be requested to start with his hand in the neutral position 602 and rotate the hand, wrist, and forearm past the supination position 600 and/or past the pronation position 604 (e.g., mimicking the pouring of water out of a glass of liquid and returning the glass to an upright position). Those of skill in the art will understand various rotations of the user's hand, wrist, and forearm suitable for prescribed motions to develop a responsiveness profile from the disclosure herein.

The base responsiveness profile is developed to detect decreases in responsiveness, alertness and/or performance of the user. As such, various parameters associated with the prescribed motion to generate the base responsiveness profile are measured to increase the accuracy and/or the reliability of responsiveness degradation detection. The parameters may include total time, reaction time, time of motion, jerk, acceleration, velocity, and/or range of motion. The base responsiveness profile may be one or more of these parameters and/or combination (e.g., an average) of one or more of these parameters.

The total time is the time lapsed from a stimulus to the completion of the prescribed motion. For example, the wearable apparatus may vibrate as a stimulus, prompting the user to perform the prescribed motion. Thus, the time lapsed from the vibration to the completion of the prescribed motion by the user is the total time as a parameter measured for the base responsiveness profile.

The reaction time is the time lapsed from a first defined event (e.g., the stimulus) to the occurrence of a second defined event. In one embodiment, the second defined event is the beginning of the prescribed motion. In another embodiment, the second defined event is a detectable response. In yet another embodiment, the second defined event is a reversal of direction during the prescribed motion. The wearable apparatus may vibrate and/or produce a sound to provide the stimulus, which prompts the user to respond (e.g., to begin the prescribed motion). Thus, the time lapsed from the vibration or sound from the wearable apparatus to the user beginning the prescribed motion may be the reaction time as a parameter measured for the base responsiveness profile.

The time of motion is the time lapsed from the beginning of a response to the end of the response (e.g., the time to perform the prescribed motion). For example, the wearable apparatus may vibrate as an indication to the user to begin the response (e.g., to begin the prescribed motion). The time lapsed from the beginning of the prescribed motion to the completion of the prescribed motion is the time of motion as a parameter measured for the base responsiveness profile.

The velocity is the rate of change of the position of the wearable device in the prescribed motion over time. For example, the prescribed motion may require the user to rotate the hand, wrist, and/or forearm. The velocity may be used as a parameter to show a decrease or increase in velocity while the user is responding to the stimulus.

The acceleration is the rate at which the velocity of the wearable apparatus in the prescribed motion changes over time. The jerk is the rate at which the acceleration of the wearable apparatus in the prescribed motion changes over time.

The range of motion is the degrees and/or amount of motion through which, for example, the wrist, hand, or forearm rotates during the prescribed motion. For example, the wearable apparatus may vibrate as the stimulus, indicating to the user to begin the prescribed motion. The amount the user rotates the hand, wrist, and/or forearm after the stimulus is the range of motion as a parameter measured for the base responsiveness profile.

The above parameters measured for the base responsiveness profile are exemplary and not exclusive. It is contemplated that other parameters, such as velocity, jerk, etc. may be measured to develop the base responsiveness profile. Other such suitable parameters will be understood by one of skill in the art from the disclosure herein. When multiple prescribed motions are performed to generate the base responsiveness profile, the parameters from the prescribed motions may be averaged to generate the parameters in the base responsiveness profile.

The base responsiveness profile should be generated when the user has a high level of alertness, such that degradation of performance and alertness can be accurately detected in future measurements. In one embodiment, the base responsiveness profile is determined in a controlled environment such as a laboratory. In use, once the wearable apparatus is in the initialization mode, the user performs the prescribed motion, and the apparatus (or mobile device, mobile application, central server, etc.) measures the total time, reaction time, time of motion, acceleration, range of motion, and/or other parameters, and stores those measured parameters (and/or an average of each parameter from multiple performances) as the baseline for the responsiveness profile. Future measurements of the parameters are compared against this baseline of the responsiveness profile to detect degradation of alertness and/or performance of the user.

At block 404, a baseline fatigue risk level may be generated by using initial measurements of one or more of the user's sleep risk variables. Sleep risk variables that may be suitable for use at this step include, but are not limited to, a location within an estimated personal circadian rhythm of the user, biomarkers of the user, and data derived from a chronotype survey of a user.

At block 406, an appropriate stimulus interval may be calculated for the user based on the base responsiveness profile and/or the baseline fatigue risk level. For example, the user may have a high base responsiveness profile, which corresponds to a longer stimulus interval because the responsiveness profile indicates a higher base level of alertness. In another example, the user may have a low base responsiveness profile, corresponding to a shorter stimulus interval due to the user's perceived lower base level of alertness. In yet another example, the baseline fatigue risk level may be incorporated into calculating an appropriate stimulus interval along with the generated base responsiveness profile.

At block 408, an alertness test is initiated by providing a stimulus to the user. The stimulus may be provided in accordance with a calculated stimulus interval. The alertness test is initiated while the user is performing the task that requires alertness (e.g., driving, studying, etc.). The alertness tests may be configured to be initiated at particular intervals. For example, the tests may be configured to initiate every 6-10 minutes, at random times during each 6-10 minute interval, and/or in response to predefined movement/non-movement (e.g., when activity level is below a predefined threshold for a predefined period of time). In an embodiment, the test may be delayed in response to predefined stimulus (e.g., a detected lane change or turn). In an embodiment, a stimulus interval may expire and a stimulus to the user is due. However, motion sensor(s) 104 sense motion at the time the apparatus 100 would otherwise issue the stimulus. The stimulus may be delayed to accommodate this period of user activity. For example, the wearable apparatus may be configured to detect motion indicative of critical vehicle operation (e.g., a lane change or turn) and, in response to this detection, delay the alertness test. In another embodiment, the wearable apparatus includes a mechanism (e.g., an external button; not shown) that permits a user to manually delay the test. The time intervals may be adjusted by the user, an administrator, and/or other entity.

An embodiment may also issue a "queuing" warning to the user to prepare the user for a stimulus. This indicates to the user that a stimulus is impending. The user may then be prepared to perform the prescribed motion when the alert stimulus is applied, which may normalize reaction and response times.

When the alertness test is initiated, the wearable device may produce a stimulus that prompts the user to respond (e.g., begin the prescribed motion). The stimulus may be a vibration of the wearable apparatus, an audio alert from the wearable apparatus, and/or alerts generated by a mobile device, mobile application, etc. In one embodiment, the prescribed motion may be changed periodically (e.g., every time, after a few times, or every six months). In one embodiment, the user may be prompted to perform one of a plurality of prescribed motions that may changes on a periodic and/or random basis. For example, one stimulus may be provided sometimes (e.g., a single relatively long vibration) to prompt the user to perform a first prescribed motion such as a motion with hand open and another stimulus may be provided at other times (e.g., two relatively short vibrations) to prompt the user to perform a second prescribed motion such as the same motion with the hand closed.

At block 410, data from the prescribed motion is gathered and a current responsiveness profile is generated from the gathered data. The data may be gathered by the wearable apparatus, mobile device, mobile application, central server, and/or a combination thereof. The data may be gathered by recording parameters from the corresponding prescribed motion that were previously used to generate the base responsiveness profile (e.g., total time, reaction time, time of motion, jerk, acceleration, range of motion, etc.). The data may be processed to generate the current responsiveness profile. For example, one or more of the parameters from the gathered data may be used to generate the current responsiveness profile. The current responsiveness profile may also be stored as an historical responsiveness profile. It is contemplated that no response may occur to the stimulus (e.g., the user performs no motion in response to the stimulus within a predetermined allowable amount of time). In such instances, the wearable apparatus, mobile application, mobile device, and/or central server, may be configured to generate an alarm indicating no response to the stimulus. The alarm may be communicated to third parties monitoring the user, and/or may be audible/visual/etc. such that the user (or other individual in the vicinity) can perceive the warning.

At block 412, the current responsiveness profile generated from the gathered date is compared to the baseline responsiveness profile generated at block 402 for the corresponding prescribed motion. In one example, one or more of the parameters measured from the response are compared to one or more corresponding parameters from the base responsiveness profile. Each parameter may be used to calculate a responsiveness value that represents the current responsiveness of the user.

At block 414, a fault to the user and/or an alert to a third party are generated if the current responsiveness profile generated from the gathered data differs by a predetermined threshold as compared to the base responsiveness profile. The predetermined threshold may be based on each parameter individually or a combination of the parameters. The threshold is determined such that differing by the threshold indicates a degradation of alertness or performance significant enough to set a fault which in turns generates a warning. In an embodiment, the warning is generated if at least one parameter in the current responsiveness profile differs by two standard deviations from the corresponding parameter in the base responsiveness profile. The warning may be provided to the user in the form of an audible, visual, or other form of perceptible alert. In an embodiment, the warning is provided to third parties in addition to or instead of the user via a mobile device, mobile application, central/remote server, etc. The time interval between alertness tests after a warning may be decreased, such that more alertness tests are conducted to monitor the alertness of the user. In such embodiments, the time interval between alertness tests reverts to the original interval once the responses of the user return within the predetermined threshold of the base responsiveness profile. The measured responses may then be stored as historical responsiveness profiles at block 416. These historical responsiveness profiles can then be used for future comparisons as described at blocks 418-422.

At block 418, the current responsiveness profile is compared to one or more stored historical responsiveness profiles (e.g., one or more historical responsiveness profiles immediately preceding the current responsiveness profile that are subsequent to the base responsiveness profile). This may occur after a current responsiveness profile is generated at block 410 and there are stored historical responsiveness profiles available. The current responsiveness profile may also be compared to the base responsiveness profile at the same time as the current responsiveness profile is being compared to one or more historical responsiveness profiles.

The previously measured responses may be stored on the wearable apparatus, mobile application, mobile device, central server, etc. A fault to the user and/or an alert to a third party may be generated if the current responsiveness profile is a significant deviation from an historical responsiveness profile, even if both responsiveness profiles are within the threshold of the base responsiveness profile described at block 414. For example, the historical response may indicate the user's responsiveness is one standard deviation above the base responsiveness profile, and the current response may indicate the user's responsiveness is one standard deviation below the base responsiveness profile (e.g., a difference of two standard deviations from the historical responsiveness profile). While both responses are within the threshold of block 414, the system may be configured such that the significant decrease in responsiveness (e.g., two standard deviations) is sufficient to generate a warning to the user and/or a third party.

At block 420, a responsiveness trend line is generated. The responsiveness trend line is generated based on the previously measured responses' historical responsiveness profiles such that the responsiveness of the user can be observed over a period of time. For example, the trend line may represent a mean of the responses previously recorded.

At block 422, a warning is generated if the trend line falls outside a predetermined threshold. In such instances, although the user's responses are sufficiently within the threshold described at block 414 such that no warning is generated based on the individual response, the responsiveness trend line may indicate a gradual decrease in responsiveness of the user over a period of time. In an embodiment, if the responsiveness decreases by a predetermined amount (e.g., about 10% of the responsiveness profile) over a period of time, the warning is generated. The warning may be generated by the apparatus, mobile application, mobile device, central server, etc., and/or by third parties monitoring the user.

In an embodiment, the system may predict when a user's alertness may diminish to a point where they should cease performing certain duties (e.g., driving a vehicle). The predictions may be based on trend information and, optionally, other information (e.g., operator age) to determine when the user's alertness will likely fall below an acceptable level. For example, the system may predict that the user is able to continue driving for a period of time (e.g., another 90 minutes), but should then rest for a period of time (e.g., four or more hours). The system may also display to the user an alertness scale and the user's position on the alertness scale to help the user make informed decisions about the user's ability to remain on-task in a safe manner.

At block 424, at least one of a number of sleep risk variables continue to be measured periodically over time after generating a baseline fatigue risk level. After an alert and/or a fault are generated at blocks 414 and/or 422, the cycle may repeat and/or continue with the sleep risk variables being continually measured. The measurements of the at least one sleep risk variable (preferably, but not limited to, current or historical response profiles for responses of the user to each stimulus, biomarkers, and location of the user within the user's personal circadian rhythm) are used to detect changes over time in the sleep risk variables measured. Based on the changes in the continually measured sleep risk variables, dynamic risk levels for the user falling asleep or reaching dangerous levels of fatigue can be generated at block 426. The dynamic risk levels generated can then be used to adjust the appropriate stimulus interval. For example, an historical or current response profile which indicates that the user's alertness is declining can be used to generate a current, dynamic risk level in conjunction with other continually measured sleep risk variables. The generated dynamic risk level can then be incorporated into the calculation of an appropriate stimulus interval, adjusting it such that the interval is shorter between stimuli to reflect the user's decreasing alertness.

Other functionalities of the disclosed systems and methods for monitoring the alertness of a user are contemplated. For example, the systems may allow for real-time monitoring of the user by third party via a mobile application or mobile device paired with the wearable apparatus, such that the third party can make real-time decisions as to whether to generate warnings. The parameters of the parameters and the thresholds may be adjustable and/or customizable in real-time and to suit particular environments (e.g., setting a more restrictive threshold on night-time driving). A plurality of prescribed motions may be used to generate the responsiveness profile, and the system may be configured to determine the user is alert when the user completes one of the plurality of prescribed motions. All functionality may be contained within the wearable apparatus, or may be divided between mobile devices and remote servers. A mobile application (e.g., a smart phone app) may be utilized to pair the wearable apparatus with a mobile device.

Figure 5:
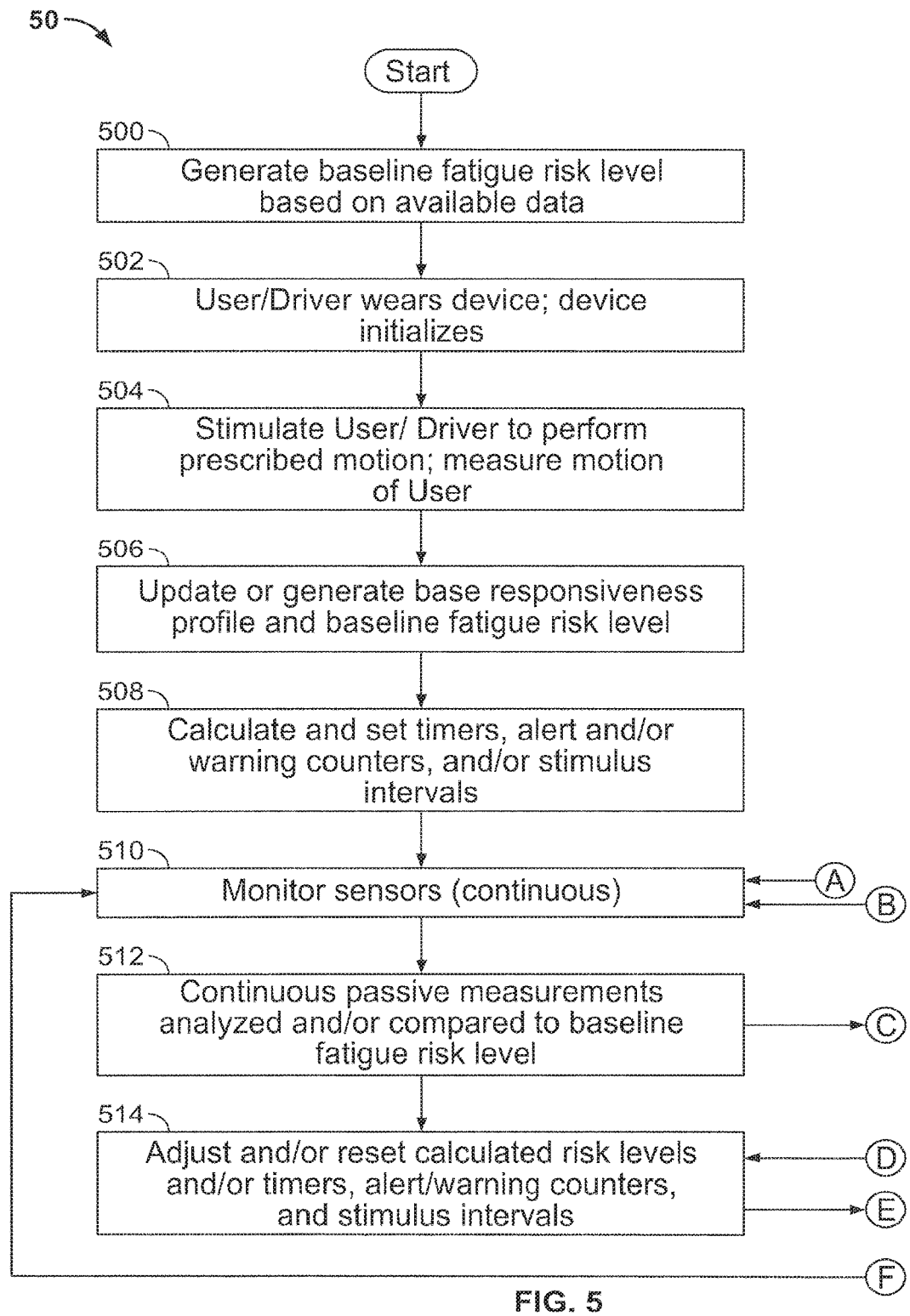
FIG. 5 is a flow chart of steps for monitoring the alertness of a user in accordance with aspects of the invention.
Figure 5:
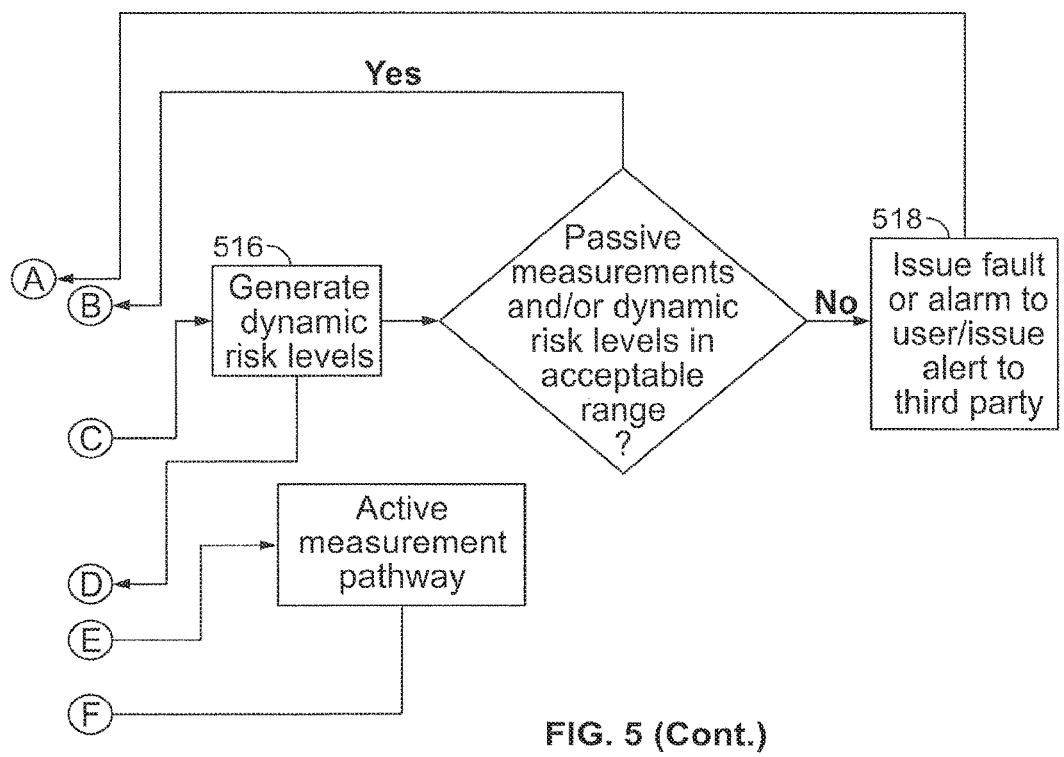

FIG. 5 depicts a flow chart 50 of steps that may be performed to monitor alertness and to notify a user wearing the apparatus or a third party that the user should go to sleep or take a nap due to high levels of fatigue. The steps of flow chart 500 are described below with reference to the components in FIGS. 1A, 1B, and 1C. Other suitable components for carrying out these steps will be understood by one of skill in the art from the description herein.

First, at step 500, a baseline fatigue risk level for the user may be generated based on any available data. Available data may include health information of the user, subjective alertness levels input by the user into the apparatus prior to wearing it or while wearing the apparatus, a sleep history input by the user into the apparatus about the duration of last sleep and the length of time elapsed since waking. In another example, the base responsiveness profile may be determined while the baseline fatigue risk is being generated.

A baseline fatigue risk level of the user may also be generated based on initially measured sleep risk variables. Sleep risk variables initially measured during the test period may include prescribed motions of the user, biomarkers detected by the biometric sensor module, or a location within an estimated personal circadian rhythm of the user. The sleep risk variables can then be used to determine the user's natural predisposition to fatigue. This predisposition can then be used to determine the user's baseline fatigue risk level.

At step 502, the user may put the apparatus on. After the apparatus is first put on it powers up and performs its initialization sequence. After initialization is complete, the system may initiate a stimulus at step 504 (e.g., a vibration) in order to prompt the wearer to perform a prescribed action. The apparatus may at step 506 capture the user's base response, generate and/or update a base responsiveness profile (if not generated previously or as an update to a previously generated base responsiveness profile) and ensure that the user can detect the stimulus. The baseline fatigue risk level may also be generated if it had not been generated previously, or the baseline fatigue risk level may be updated.

At step 508, alert/warning counters, stimulus intervals, and timers are calculated and set to their starting values. The count-down timer for the primary motion monitoring loop is initialized and started. A generated baseline fatigue risk level may be incorporated into the calculation of a count-down timer and an appropriate stimulus interval for alerting the user to perform a prescribed motion. Additionally, an appropriate stimulus interval may be calculated based on a combination of both the base responsiveness profile and the baseline fatigue risk level of the user.

At step 510, apparatus may continuously and/or periodically monitor the signals from both the motion sensors indicating general movement of the user (passive measurements of motion) and biomarker signals received from the biometric sensor module (passive biometric measurements). Signals from both the motion sensor(s) and/or the biometric sensor module may be continually monitored during the time that the user is wearing the apparatus to obtain passive ongoing measurements of the user's fatigue.

The continuous and/or periodic passive measurements of user motion and biomarkers may be analyzed and/or compared to a baseline fatigue risk levels at step 512. A previously determined threshold for one or more of the passive measurements may be used to determine if the passive measurements indicate a severe increase in fatigue. If the passive measurements analyzed exceed the threshold, then the measurements may be considered to exceed acceptable ranges of fatigue. The continuous and/or periodic passive measurements can also be used to adjust alert/warning counters, stimulus intervals, and timers. The active measurement pathway involved user stimulus and response may then continue. For example, the active measurement pathway as depicted in FIG. 3 may be carried out.

Additionally, continuous and/or periodic passive measurements of motion and biomarkers may be used to generate dynamic risk levels for user fatigue at step 516. The measurements may be obtained by continually measuring the user's sleep risk variables, including biomarkers sensed by the biometric sensor module, after generating a baseline fatigue risk level and/or base responsiveness profile. Changes over time in different sleep risk variables may be incorporated into calculations of dynamic risk levels. These current dynamic risk levels may then be used to continually recalculate and adjust the stimulus intervals and/or count-down timers at step 514. For example, as changes in a sleep risk variable occur to indicate increasing fatigue risk of the user, new dynamic risk levels can be generated to reflect the increased risk. From step 514, the steps of the active measurement pathway may continue (see FIG. 3 for an example), and may lead back to continuous monitoring of sensors at block 510.

The flow of operational logic is such that a determination is made about whether dynamic risk levels and/or passive measurements are within an acceptable range of fatigue. This may include determining whether passive measurements exceed a predetermined threshold and/or determining whether dynamic risk levels indicate severe fatigue in the user. Should the passive measurements and/or dynamic risk levels be within an acceptable range, the apparatus may simply continue to monitor the biometric sensor module and motion sensor(s) passively at step 510. However, if the passive 3o measurements and/or dynamic risk levels fall outside an acceptable range, an alarm or fault may be issued to the user to engage in a period of sleep (e.g. a nap) to avoid any issues or danger resulting from fatigue (see step 518). In one embodiment, an alert may be issued to a third party, e.g. a dispatcher, indicating that the user should engage in sleep to prevent danger resulting from fatigue (see step 518). This may provide a third party with an opportunity to communicate with the user to further emphasize the user's need for rest or sleep.

Figure 7:
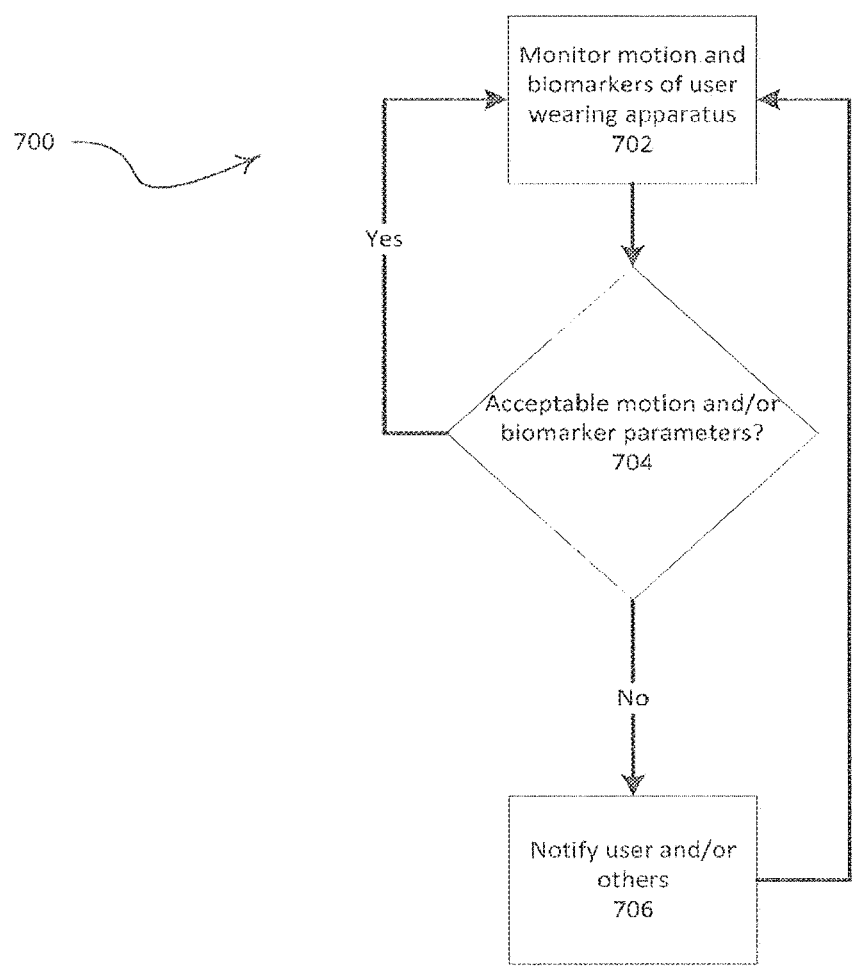
FIG. 7 depicts a flow chart of steps for monitoring alertness of a user in accordance with aspects of the invention.

FIG. 7 depicts a flow chart 700 of steps that may be performed to monitor alertness and notify a user wearing a wearable device that is exhibiting signs of diminished alertness (e.g., fatigue). The steps of flow chart 700 are described below with reference to the components in FIGS. 1A, 1B, and 1C. Other suitable components for carrying out these steps will be understood by one of skill in the art from the description herein.

At step 702, the motion of a user/wearer may be monitored. The processor 108 may monitor the temperature and motion outputs from motion sensor 104 and biometric sensor module 105 (e.g., from temperature sensors/motion sensors/gyroscopes/accelerometers). The temperature sensor and/or capacitive touch sensor may be used to determine whether the apparatus 100 is actually being worn against the skin of the user. The motion outputs may be used to monitor the motion of the wearable apparatus 100.

At step 704, the monitored motion and/or biomarkers are assessed to determine whether there is acceptable motion and/or biological indications of alertness. The acceptable motion may be assessed by comparing information received from motion sensor 104 to a parameter or parameters by the processor 108. The acceptable biological indications of alertness may be assessed by comparing information received from biometric sensor module 105 to a range or parameters by the processor 108. The parameter may be lack of significant motion for 10 seconds (indicating the user has fallen asleep due to fatigue). There may be other suitable lengths of time for determining lack of significant motion. The parameter may also be, for example, a significant increase in distal skin temperature.

Other algorithms may be employed to determine that the user is fatigued. The clock 112 may be capable of measuring time to allow for both the determination of the expiration of a main monitoring cycle, as well as the measuring an operator's response time. The operator's response times as well as recorded temperatures and times may be stored in memory 110, e.g., so that a dispatcher can later verify that the wearable apparatus 100 was being properly worn in the event that a telematic system is not available to communicate.

The processor 108 may be configured to discriminate between movement of the user and other movement, e.g., movement of a vehicle such as a truck. This may be accomplished, by way of non-limiting example, tracking relatively small radius angular movements. Examples of these movements include the rotation of the wrist, the curling of the arm at the elbow, the swinging of the arm from the shoulder, or the rotation of the hands around the steering wheel. All of these types of movements produce an angular rotation angle that is too small for the cab of a truck to make when turning or through any normal movement of the truck. In addition, by looking for angular movements, the device can ignore linear acceleration such as is caused by uneven pavement, riding over a vertical displacement in the road, or those caused by the buffeting of wind against the truck.

The processor 108 may be programmed to identify angular motion whose radius of motion is between 1-centimeter and 200-centimeters based on input from the motion sensors 104a. The low end of the range removes small angular shifts due to vibration from consideration and the high end of the range removes large scale radial motion, such as from a turning truck, for example, from consideration.

If acceptable motion by the user is not detected, at step 806, the user wearing the wearable apparatus 100 is notified. A vibration device within the wearable apparatus 100, such as an offset weight spinner, and/or an audio tone generator may provide reminder signals and alerts to the user. Others associated with the user (e.g., employers/teachers/parents) may also be notified. The transceiver 114 may be used to notify a telematic device or a smart phone application in the event of any operator alerts.

In the case of a vehicle operator, the system may process out the measured normal movements of the vehicle and look for discernible movements, such as shifting, tuning the radio, drinking, or even an intentional wrist shake. If the operator goes some period without making any of these discernible movements, a fault would be generated resulting in an unobtrusive warning that would signal the operator that he must make a movement—an intentional wrist shake, for example. This would restart the motion monitoring loop. In addition, it would record the response time between the warning signal and the detected motion. If the operator does not make a discernible movement in a reasonable amount of time or the operator's response time is continually degrading (a symptom of fatigue), the system then issues an alarm perceptible to the operator (and optionally others in the vicinity of the operator), suggesting he might be too tired to drive. If connected to a telematics system, this alert could also be sent to the dispatcher, for example.

In an embodiment of the present invention, the apparatus 100 may also be used by a third party, such as law enforcement, to determine if a user, such as a driver, is at a minimum alertness level to engage in an activity such as driving. The apparatus 100 could therefore be used as an alternative to a breathalyzer to measure driver fitness for operating a vehicle. Alertness levels may be affected by different issues, such as use of alcohol, drugs, medical issues, and fatigue. These issues can cause a driver to decline in alertness to such an extent that the driver may be considered "impaired." The apparatus 100 could therefore determine a user/driver's alertness to establish whether the user/driver is impaired, and the user/driver's impairment status could be used by law enforcement as an alternative to a breathalyzer.

The apparatus 100 and its components may also be used to detect if and when a user wearing the apparatus has fallen. Using the one or more motion sensor(s) 104, the apparatus 100 may determine that a user has fallen by detecting a quick acceleration toward the ground, or with the pull of gravity. The apparatus may be configured to send an alert to a third party, e.g. a dispatcher, to apprise the third party of the user's fallen status. This would allow the third party to send emergency personnel or to establish contact with the user to determine the health or status of the user.

The apparatus 100 may be configured to wake a user up from a nap or sleeping period. For example, the apparatus 100 may detect when a user falls asleep based on passive biometric and motion measurements and thereafter wake the user up using an alarm at a predetermined duration of sleep (e.g. 20 minutes). The user may also input a desired nap time prior to going to sleep, and the apparatus 100 may be configured to issue an alarm to the user upon the expiration of that time. In another embodiment, the apparatus 100 may determine an optimal time to wake the user up with an alarm based upon the detection that the user has fallen asleep and the detection of passive biometric and motion measurements. The passive measurements may be used to determine the user's position in a circadian rhythm and/or to determine the user's position within the user's REM sleep cycle to ascertain an optimal time to wake the user.

The apparatus 100 may also be configured for use as a tool to improve fitness of a user. The components of the apparatus 100 may be used to measure movements and various biomarkers of the user to indicate physical activity and periods of rest. For example, the user's heart rate may be monitored during physical activity (e.g. exercise) 2s to help bolster the user's attempt to improve fitness and to monitor progress. The movements monitored may be used to determine the level of vigor used during physical activity. The apparatus 100 may be in the form of a watch.

The apparatus 100 may incorporate machine learning techniques to detect events such as decreased alertness and/or sleep of a user. Machine learning techniques refer to using neural networks and/or other pattern recognition techniques to train the system or apparatus 100 to detect different events by incorporating linear and non-linear variables. The machine learning techniques may aggregate variables to determine and generate baseline fatigue risk levels, dynamic risk levels, and/or base responsiveness profiles.

The apparatus 100 may also be used at a fatigue management tool to help the user reduce fatigue during waking hours. By looking at changes in the user's risk levels of falling asleep over a period of time, along with other data provided by the apparatus 100, the apparatus 100 can be used as a tool during fatigue management training to monitor progress. As the user monitors his or her sleep patterns and/or fatigue during day time activities with the apparatus 100, the apparatus 100 can provide the user or a third party with information regarding the user's daily and real time fatigue data. The apparatus 100 can also monitor and track improvements in the user's sleep drive, sleep debt, sleep duration, and sleep quality, and the improvements may be shared with the user or a third party.

Although the invention is illustrated and described herein with reference to specific embodiments, the invention is not intended to be limited to the details shown. Rather, various modifications may be made in the details within the scope and range of to equivalents of the claims and without departing from the invention.

What is claimed is:

1. A system for monitoring fatigue and notifying a user, the system comprising:
   a wearable apparatus comprising:
      a sensor configured to measure biomarkers of the user;
      a communication module; and
      a support configured to support the sensor; and
   a remote device comprising:
      memory;
      a notification generator configured to generate a warning to the user via the communication module in response to receipt of a signal;
      a processor communicatively coupled to the sensor and the notification generator, the processor configured to:
         obtain, from the communication module, biomarker measurements from the sensor;
         generate a personal circadian rhythm for the user, and a position of the user along that circadian rhythm, using the measured biomarkers;
         identify a baseline risk level for the user by assessing the personal circadian rhythm of the user and the position of the user along that personal circadian rhythm;
         determine a sleep drive of the user based upon continual or periodic sensor measurements, wherein sleep and wakefulness cycles of the user are derived from actigraphy data obtained from the sensor; and
         send the signal to the notification generator when the baseline risk level is in a predetermined range.

2. The system of claim 1, wherein the processor is further configured to:
   generate a mask event of the personal circadian rhythm based upon changes in body position or activity of the user; and
   remove the mask event from a personal circadian rhythm estimate by scaling data from the personal circadian rhythm to correct for body position as measured by the sensor and averaging personal circadian rhythm data in a testing period.

3. The system of claim 2, wherein the processor is further configured to:
   scale the personal circadian rhythm data to generate corrected data for an activity of the user during the testing period as measured by the sensor; and
   generate a more accurate estimate of the personal circadian rhythm based on the corrected data.

4. The system of claim 1, wherein the processor is further configured to generate the personal circadian rhythm, and the position of the user along that personal circadian rhythm, based upon a skin temperature of the user as measured by the sensor.

5. The system of claim 4, wherein the processor is further configured to generate the personal circadian rhythm by correlating a distal skin temperature of the user to a core body temperature of the user.

6. A method for monitoring fatigue and notifying a user, comprising:
   affixing on the user an apparatus comprising a sensor and a communication module, wherein the sensor is in communication, via the communication module, with a notification generator and a processor configured to detect and monitor biomarkers of the user;
   generating, by the processor, an estimated personal circadian rhythm for the user based upon measured biomarkers;
   determining, by the processor, a dynamic risk level for the user based on the estimated personal circadian rhythm of the user, and a position of the user along that estimated personal circadian rhythm;
   determining, by the processor, a sleep drive of the user based upon continual or periodic sensor measurements, wherein sleep and wakefulness cycles of the user are derived from actigraphy data obtained from the sensor; and
   sending a signal to the notification generator when an identified risk level is in a predetermined range such that the notification generator outputs an alert.

7. The method of claim 6, further comprising:
   generating a mask event of the estimated personal circadian rhythm based upon changes in body position or activity of the user; and
   removing the mask event from the estimated personal circadian rhythm by scaling data from the circadian rhythm to correct for body position as measured by the sensor and averaging the circadian rhythm data in a testing period.

8. The method of claim 7, further comprising:
   scaling the circadian rhythm data to generate corrected data for an activity of the user during the testing period as measured by the sensor; and generating a more accurate estimate of the personal circadian rhythm based on the corrected data.

9. The method of claim 6, wherein one of the biomarkers is skin temperature.

10. The method of claim 6, wherein biomarker measurements relied upon to determine the dynamic risk level are made at the sensor.

11. The method of claim 10, wherein the sensor is located on a distal portion of the user.

12. A wearable device for monitoring fatigue comprising:
a sensor configured to measure biomarkers and actigraphy data of a user, wherein the sensor is communicatively coupled to:
a remote device comprising memory and a processor; and
a notification generator configured to generate a warning to the user in response to receipt of a signal; and
a communication module configured to:
output, to the remote device, biomarker measurements from the sensor;
receive, from the remote device:
personal circadian rhythm for the user, and a position of the user along that circadian rhythm, using the measured biomarkers;
a baseline risk level for the user by assessing the personal circadian rhythm of the user and the position of the user along that personal circadian rhythm; and
a sleep drive of the user based upon continual or periodic sensor measurements, wherein sleep and wakefulness cycles of the user are derived from actigraphy data obtained from the sensor; and
receive, from the notification generator, the signal when the baseline risk level is in a predetermined range; and
a support configured to support the sensor and the communication module.

13. The wearable device of claim 12, wherein the communication module is further configured to:
generate a mask event of the personal circadian rhythm based upon changes in body position or activity of the user; and
remove the mask event from a personal circadian rhythm estimate by scaling data from the personal circadian rhythm to correct for body position as measured by the sensor and averaging personal circadian rhythm data in a testing period.

14. The wearable device of claim 13, wherein the communication module is further configured to:
scale the personal circadian rhythm data to generate corrected data for an activity of the user during the testing period as measured by the sensor; and
generate a more accurate estimate of the personal circadian rhythm based on the corrected data.

15. The system of claim 12, wherein the communication module is further configured to generate the personal circadian rhythm, and the position of the user along that personal circadian rhythm, based upon a skin temperature of the user as measured by the sensor.

16. The system of claim 15, wherein the communication module is further configured to generate the personal circadian rhythm by correlating a distal skin temperature of the user to a core body temperature of the user.

17. A method for monitoring fatigue, comprising:
affixing on a user a wearable device comprising a sensor and a communication module;
measuring, by the sensor, biomarkers and actigraphy data from the user;
outputting, by the communication module, the biomarkers and actigraphy data from the wearable device to a remote device;
receiving, at the sensor, personal circadian rhythm for the user, and a position of the user along that circadian rhythm, using the measured biomarkers;
receiving, at the communication module, a baseline risk level for the user by assessing the personal circadian rhythm of the user and the position of the user along that personal circadian rhythm; and
receiving, at the sensor, a sleep drive of the user based upon continual or periodic sensor measurements, wherein sleep and wakefulness cycles of the user are derived from actigraphy data obtained from the sensor; and
receiving at the communication module, from (i) the remote device or (ii) a third party device that is remote with respect to the wearable device and the remote device, a signal based upon an identified risk level being in a predetermined range such that a notification generator outputs an alert.

18. The method of claim 17, further comprising:
generating a mask event of the estimated personal circadian rhythm based upon changes in body position or activity of the user; and
removing the mask event from the estimated personal circadian rhythm by scaling data from the circadian rhythm to correct for body position as measured by the sensor and averaging the circadian rhythm data in a testing period.

19. The method of claim 18, further comprising:
scaling the circadian rhythm data to generate corrected data for an activity of the user during the testing period as measured by the sensor; and
generating a more accurate estimate of the personal circadian rhythm based on the corrected data.

20. The method of claim 17, wherein one of the biomarkers is skin temperature.

21. The method of claim 17, wherein biomarker measurements relied upon to determine the dynamic risk level are made at the sensor.

22. The method of claim 21, wherein the sensor is located on a distal portion of the user.

23. A computing device for monitoring fatigue, the computing device comprising:
memory;
a notification generator configured to generate a warning in response to receipt of a signal;
a communication module; and
a processor communicatively coupled to the notification generator and, via the communication module, to a user device worn by a user, the processor configured to:
obtain, by the communication module, biomarker measurements about the user from a sensor in the user device;
generate a personal circadian rhythm for the user, and a position of the user along that circadian rhythm, using the measured biomarkers;
identify a baseline risk level for the user by assessing the personal circadian rhythm of the user and the position of the user along that personal circadian rhythm;
determine a sleep drive of the user based upon continual or periodic sensor measurements, wherein sleep and wakefulness cycles of the user are derived from actigraphy data obtained from the sensor; and output, by the communication module, the signal to the notification generator when the baseline risk level is in a predetermined range.

24. The computing device of claim 23, wherein the processor is further configured to:

generate a mask event of the personal circadian rhythm based upon changes in body position or activity of the user; and remove the mask event from a personal circadian rhythm estimate by scaling data from the personal circadian rhythm to correct for body position as measured by the sensor and averaging personal circadian rhythm data in a testing period.

25. The computing device of claim 24, wherein the processor is further configured to:

scale the personal circadian rhythm data to generate corrected data for an activity of the user during the testing period as measured by the sensor; and generate a more accurate estimate of the personal circadian rhythm based on the corrected data.

26. The system of claim 23, wherein the processor is further configured to generate the personal circadian rhythm, and the position of the user along that personal circadian rhythm, based upon a skin temperature of the user as measured by the sensor.

27. The system of claim 26, wherein the processor is further configured to generate the personal circadian rhythm by correlating a distal skin temperature of the user to a core body temperature of the user.

28. A method for monitoring fatigue, comprising:

receiving at a communication module in a first device, from a wearable device worn by a user and communicatively coupled to the first device, biomarkers and actigraphy data from the user;

generating, by a processor in the first device, an estimated personal circadian rhythm for the user based upon measured biomarkers;

determining, by the processor, a dynamic risk level for the user based on the estimated personal circadian rhythm of the user, and a position of the user along that estimated personal circadian rhythm;

determining a sleep drive of the user based upon continual or periodic measurements from a sensor, wherein sleep and wakefulness cycles of the user are derived from actigraphy data obtained from the sensor; and outputting, from the communication module to (i) the user-worn device or (ii) a third party device that is remote with respect to both the first device and the wearable device, a signal when an identified risk level is in a predetermined range.

29. The method of claim 28, further comprising:

generating a mask event of the estimated personal circadian rhythm based upon changes in body position or activity of the user; and removing the mask event from the estimated personal circadian rhythm by scaling data from the circadian rhythm to correct for body position as measured by the sensor and averaging the circadian rhythm data in a testing period.

30. The method of claim 29, further comprising:

scaling the circadian rhythm data to generate corrected data for an activity of the user during the testing period as measured by the sensor; and generating a more accurate estimate of the personal circadian rhythm based on the corrected data.

31. The method of claim 28, wherein one of the biomarkers is skin temperature.

32. The method of claim 28, wherein biomarker measurements relied upon to determine the dynamic risk level are made at the sensor.

33. The method of claim 32, wherein the sensor is located on a distal portion of the user.

* * * * *